United States Patent
Sato et al.

(10) Patent No.: US 6,391,238 B1
(45) Date of Patent: May 21, 2002

(54) METHOD OF PRODUCING ALGAE CULTIVATING MEDIUM

(75) Inventors: Tatsuaki Sato, Tokyo; Shinya Miyamoto, Hitachinaka; Masumitsu Toyohara, Yokohama; Masaru Okamoto; Yoshinari Takamatsu, both of Kawasaki, all of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/438,768

(22) Filed: Nov. 12, 1999

(30) Foreign Application Priority Data

Nov. 13, 1998 (JP) .......................................... 10-323869

(51) Int. Cl.$^7$ .................... B29C 47/00; B29C 43/00; C05D 9/00
(52) U.S. Cl. .............. 264/141; 264/177.11; 264/211.11; 264/319; 71/32; 71/54; 71/64.04
(58) Field of Search ................................ 264/141, 157, 264/140, 177.11, 209.3, 211.11, 319; 71/64.04, 32, 54, 31, 35, 900, 904

(56) References Cited

U.S. PATENT DOCUMENTS

| | | | | |
|---|---|---|---|---|
| 4,235,043 A | * | 11/1980 | Harasawa et al. | 47/1.4 |
| 4,236,349 A | * | 12/1980 | Ramus | 47/1.4 |
| 5,292,461 A | * | 3/1994 | Juch et al. | 23/313 R |
| 5,433,173 A | * | 7/1995 | Markles, Jr. | 119/231 |
| 5,967,087 A | * | 10/1999 | Markels, Jr. | 119/215 |

FOREIGN PATENT DOCUMENTS

| | | | |
|---|---|---|---|
| JP | 64-52050 | | 2/1989 |
| JP | 2-115039 | | 4/1990 |
| JP | 10-94341 | | 4/1998 |
| JP | 11-243943 | | 9/1999 |
| JP | 2000-245278 | * | 9/2000 |

* cited by examiner

Primary Examiner—Mark Eashoo
(74) Attorney, Agent, or Firm—Finnegan, Henderson, Farabow, Garrett & Dunner, L.L.P.

(57) ABSTRACT

Raw material of algae cultivating medium molded body is manufactured by mixing a mixture containing inorganic material, curing material and algae cultivating nutriment, molding the mixture to molded bodies and curing the molded bodies. The molded bodies are manufactured such that the molded bodies are water floatable having a closed cavity inside the body, or containing density decreasing material for example. The manufacturing method enables to produce algae cultivating medium that can float on water in a large quantity. Industrial waste such as coal ashes and incineration ashes, sands and crushed shells can be used as the inorganic raw material of the medium. As the curing material which solidify the molded body, other than cement, algae cultivating nutriment such as phosphorus compounds can be used. Extrusion molding can favorably be applied for molding molded body. A cylindrically molded body can be sealed the both edges thereof to form a cavity portion inside thereof. A disintegration molding after preparatory molding, or agitation molding can also be used as molding step of this manufacturing method. Further, waste heat of a thermal power plant or an incinerator that produce inorganic material as wastes can be used for curing the molded body.

20 Claims, 14 Drawing Sheets

METHOD OF PRODUCING ALGAE CULTIVATING MEDIUM

BACKGROUND OF THE INVENTION

1. Field of the Invention

The present invention relates to a method of producing algae cultivating medium for cultivating algae on a large scale in seas and lakes. In particular the present invention relates to a method of producing nutriment supply medium for cultivating algae through the effective use of coal ashes or incineration ashes generated from thermal power plants or incinerators, or sands or crushed shells.

2. Description of the Related Art

Microscopic algae having high sunlight utilization ratio per unit area show high $CO_2$ fixation ability compared with plants on land. Accordingly, cultivating algae is regarded as a promising procedure for fixing $CO_2$ in the air. For this reason, there have been studies for utilizing microscopic algae absorbing and fixing $CO_2$ studies as a method of preventing the global warming up, in addition to some development works for producing useful products such as substitute fuel for oil from the cultivated algae.

Studies for cultivating microscopic algae in a photo-reactor have been performed in many research laboratories where exhaust gas rich in $CO_2$ is carried from a thermal power plant to the photo-reactor in which sunlight can be efficiently irradiated by concentrating the light.

In order to fix so much amount of $CO_2$ as a level quantity contributing to prevent the global warming by cultivating algae, it is required to cultivate the algae in a huge area. According to a trial calculation, cultivating algae in an area of a square having a side of about 300 km is necessary to fix 10% of $CO_2$ generated in Japan.

Since such a huge area is not available in an inland area in Japan, a large-scale cultivating is limited to carry out in the oceans. In the oceans, however, an efficient supply of nutriments has been difficult. When nutriments for the algae are sprayed in the oceans, the nutriments rapidly spread out in the oceans. Accordingly, almost all of the nutriments are not used for cultivating the algae but induce eutrophication and contamination of the entire oceans.

Accordingly, a medium which fixes the nutrients at the surface of the oceans and supplies the nutrients in accordance with the increase of the algae. Some of the present inventors submitted a patent application (Japanese Patent Application No. 10-52050) relating to manufacture of a medium capable of floating on water and supplying the nutriment. The application is a result of widely studying the way for supplying nutrient to the algae in the ocean.

The manufacturing of the medium that can supply the nutriment to cultivate the algae in the oceans or the like became possible as a result of the invention described above. The medium described in the patent application (Japanese Patent Application No. 10-52050), however, contains water repellent in an appreciable quantity to have floating ability in water. The water repellent is the most expensive among the raw materials of the medium. In addition, the water repelling ability of the medium gradually deteriorates, and the medium become unable to float in water when the medium is kept floating over long period.

SUMMARY OF THE INVENTION

The present invention is carried out to solve the problem described above. An object of the present invention is to provide a method for manufacturing inexpensively a large quantity of algae cultivating medium that floats in water and works as nuclei for cultivating the algae. Industrial waste such as coal ashes from thermal power plants, incineration ashes, sands, crushed shells or the like is utilized as raw materials of the medium. The volume produced algae cultivating medium by the method can cleanly cultivate the algae by dispersing in a huge ocean area.

The method of manufacturing an algae cultivating medium in the present invention comprises the steps of mixing raw material including an inorganic material, a curing material, and an algae cultivating nutriment to form a mixture, molding the mixture into a molded body, and curing the molded body. These steps are carried out so that the algae cultivating medium is water floatable.

In the present invention, the molded body is preferably manufactured so that the density of the molded body is 1 $g/cm^3$ or less thereof for floating on water.

According to the present invention, algae cultivating medium that can float on the seawater and fresh water can be manufactured in a large quantity.

In the present invention, the molding step can comprise the steps of charging the mixture into a mold to form a preparatory molded body, and disintegrating the preparatory molded body to fine molded bodies. In this case, curing of the preparatory molded body preceding the disintegrating step can be carried out up to a level appropriate to the disintegration. Further curing can be implemented after the disintegration. A large volume of molded body can be rapidly manufactured by this method since the charging the mixture into the mold one by one is not needed.

A high-speed blade mixer having agitating blades revolving at high speed in a mixing tank can be favorably used in the present invention since homogeneous mixing can be obtained in a short time. By using a tank having approximately cylindrical shape and by placing agitating blades at the bottom thereof, the agitation and mixing are carried out very efficiently. A blade type mixer is particularly preferable as the agitating blades in order to obtain rapid mixing.

The molding step of the present invention can comprise a process of molding a molded body by agitating the mixture while spraying liquid selected from the group consisting of water and an aqueous solution of a curing material to the mixture. Curing process after the molding step can enhance the strength of the molded body. According to the present method, a huge volume of granular molded bodies can be formed in a lump. This molding process can be carried out after the mixing process continuously using a high-speed blade mixer for both mixing and molding. Of course we can use one mixer for mixing and another mixer for molding, however, we can eliminate wastes of time, labor and loss of the mixture at the transfer process by using the same mixer.

The molding step of the present invention can comprise a step of extruding a molded body by transferring the mixture to a die. According to this molding step, the molded bodies of prescribed shape can be manufactured in a huge quantity with good productivity.

The extruding step in the present invention can use a double tube or jacketed tube die. Further, the step can comprise the steps of extruding the mixture by transferring the mixture between an inner wall of an outside tube and an outer wall of an inside tube of the double tube. The step can further comprise sealing both edges thereof by cutting to form a molded body having a porous outside material layer and an inside cavity portion thereof.

Here, the cavity portion means a closed cavity without an inlet and an outlet. Apparent specific gravity of the molded body can be made small enough advantageous for the algae cultivating medium for floating on water surface.

The step for molding the molded body having an inside cavity can comprise the step of providing a low water permeability layer compared with the porous outside material layer between the porous outside material layer and the inside cavity portion.

The step of providing the low water permeability layer can be conducted by extruding by charging the porous material between an outermost tube and an intermediate tube of a die constituted by a three-fold tube and low water permeability material between the intermediate tube and an innermost tube thereof, and thereafter compressing and sealing off both edges thereof.

The low water permeability layer can contain at least one low water permeability material selected from the group consisting of coal ashes, incineration ashes, montmorillonite, kaolinite, cement, water glass, lime, and gypsum.

By employing these materials, the surroundings of the cavity portion can be made airtight. The molded body having a closed cavity surrounded by the airtight low water permeability layer can be made water floatable without containing density decreasing material by adjusting apparent density of the molded body.

The molding step of the present invention can comprise a step of compressing the mixture for forming a molded body. According to this molding method, the molded body of prescribed shape can be manufactured in a large quantity with good productivity.

The inorganic material in the present invention can be at least one selected from the group consisting of coal ashes, incineration ashes, sands, crushed shells, and diatomite. Among these, the coal ashes and incineration ashes are particularly preferable because they are industrial wastes that are produced in a huge quantity and their reuse is eagerly required.

The inorganic material at least one selected from the group consisting of coal ashes, incineration ashes, sands and crushed shells and diatomite can favorably be controlled not to contain components that pollute environment such as heavy metals and poisonous organic materials. The inorganic material can be subjected to a treatment for reducing or eliminating a component that pollutes environment such as heavy metals and poisonous organic materials. The coal ashes which is consisting essentially of stable oxide silica and alumina, can be used by managing to be free from the environment pollution components. The incineration ashes also can be used, eliminating environment pollution components at the stage of segregated collection or after-treatment of incineration ashes.

The curing material in the present invention can be at least one kind selected from cement, water glass, lime and gypsum. The curing material in the present invention can solidify the molded body while curing. The curing material can contain algae cultivating nutriment, for instance, phosphate compound as its constituent component.

The algae cultivating nutriment in the present invention can be one that contains at least one kind selected from phosphorus, nitrogen and iron is preferable. Nutriments for cultivating algae can be supplied from the medium containing the nutrient.

The raw material in the present invention can comprise at least 5 parts by weight of the curing material, and not more than 20 parts by weight of the algae cultivating nutriment, relative to 100 parts by weight of the inorganic material.

When the amount of the curing material is 5 parts by weight or more, desirable hardness can be obtained. In addition, the favorable amount of the algae cultivating nutriment is 20 parts by weight or less, since the algae increasing rate does not saturate at the amount.

In the present invention, the raw material can further comprise a density decreasing material in order that the algae cultivating medium be water floatable. The density decreasing material in the present invention can be at least one selected from the group consisting of alumina powder, pearlite, shirasu, shirasu balloon, or granular pumice stone, and diatomite. The density decreasing material can favorably be contained 10 parts by weight or more for decreasing the specific gravity of the molded body small enough to be water floatable.

The high-speed blade mixer in the present invention can preferably have a mixing tank of which bottom portion is tilted towards an exhausting outlet thereof. Productivity of the mixing process can be improved since mixer tank with tilted bottom portion easily exhausts the mixture.

The curing step in the present invention can comprise the curing of the molded body under heating. The curing under heating can be preferably carried out at temperatures of 100° C. or more. Waste heat from a thermal power plant or a waste incinerator can be preferably used as a heat source of the curing under heating. Then waste heat is effectively used and an additional heat source for curing is not required.

According to the method of manufacturing algae cultivating medium of the present invention in which primary raw material is inorganic material, the molded body medium that can be floated on water surface and can cultivate algae is manufactured in a large quantity in a short time and in low cost. The algae can be cultivated in a large quantity inexpensively by dispersing on the oceans or the like the cultivating medium produced by utilizing the industrial wastes such as coal ashes, incineration ashes or the like as the principal raw material. While eutrophication and pollution of the oceans or the like can be avoided, and reduction of $CO_2$ in the atmosphere which contributes to the prevention of the global warming up can be obtained. Further, the cultivated algae can be used as raw material of useful products such as alcohol or the like which can be used as a substituting energy source of fossil fuels. Accordingly, the present invention largely contributes in solving the environment and energy problem that the human race will encounter in the future.

DESCRIPTION OF THE PREFERRED EMBODIMENTS

In the following, modes of implementation of the present invention will be explained with reference to embodiments.

Embodiment 1

Figure 1:
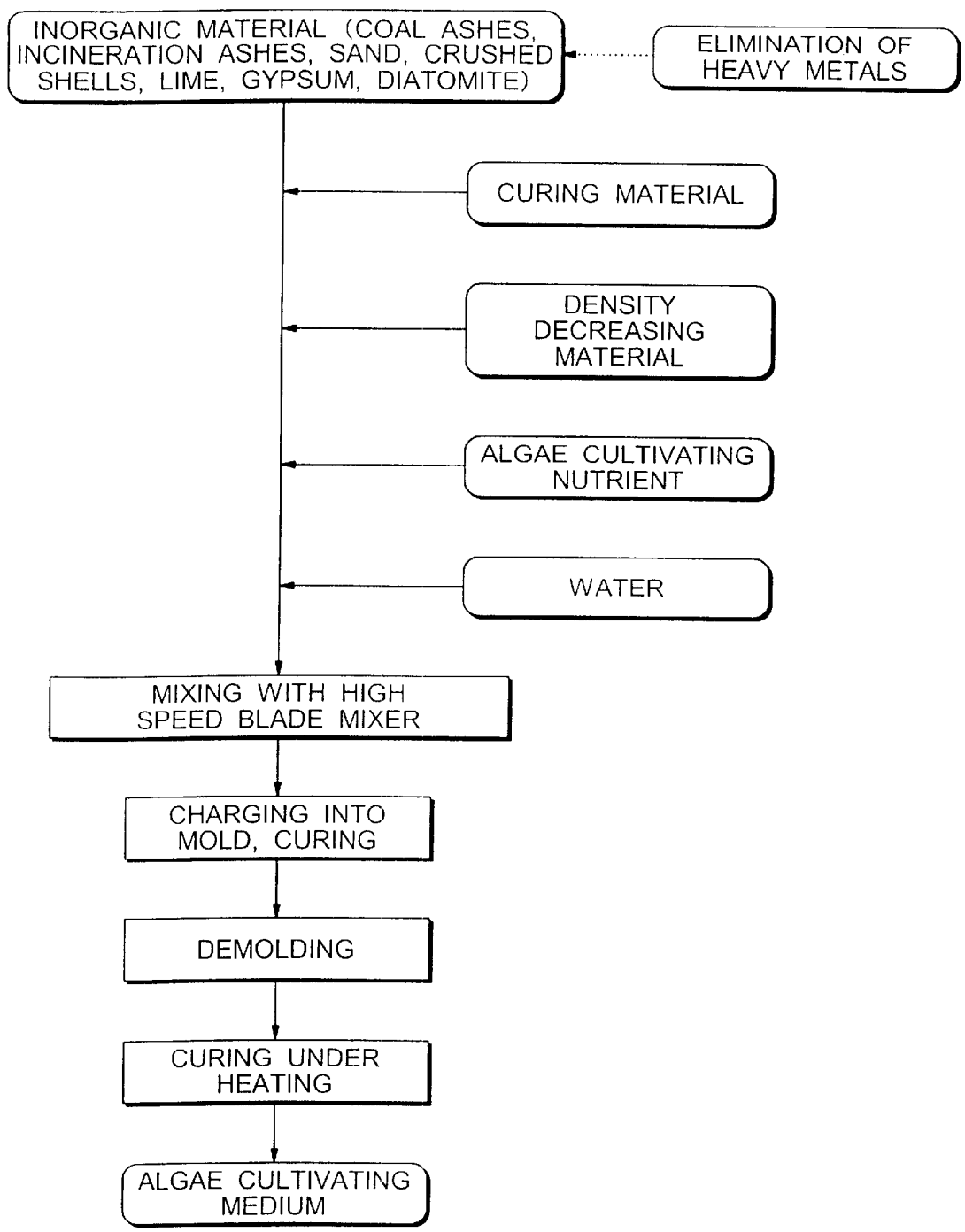
FIG. 1 is a flow-chart of a manufacturing process of an algae cultivating medium according to a standard molding method disclosed in Embodiment 1 in which inorganic material is primary raw material.

FIG. 1 shows a standard molding process of algae cultivating media in Embodiment 1 of the present invention.

Figure 2:
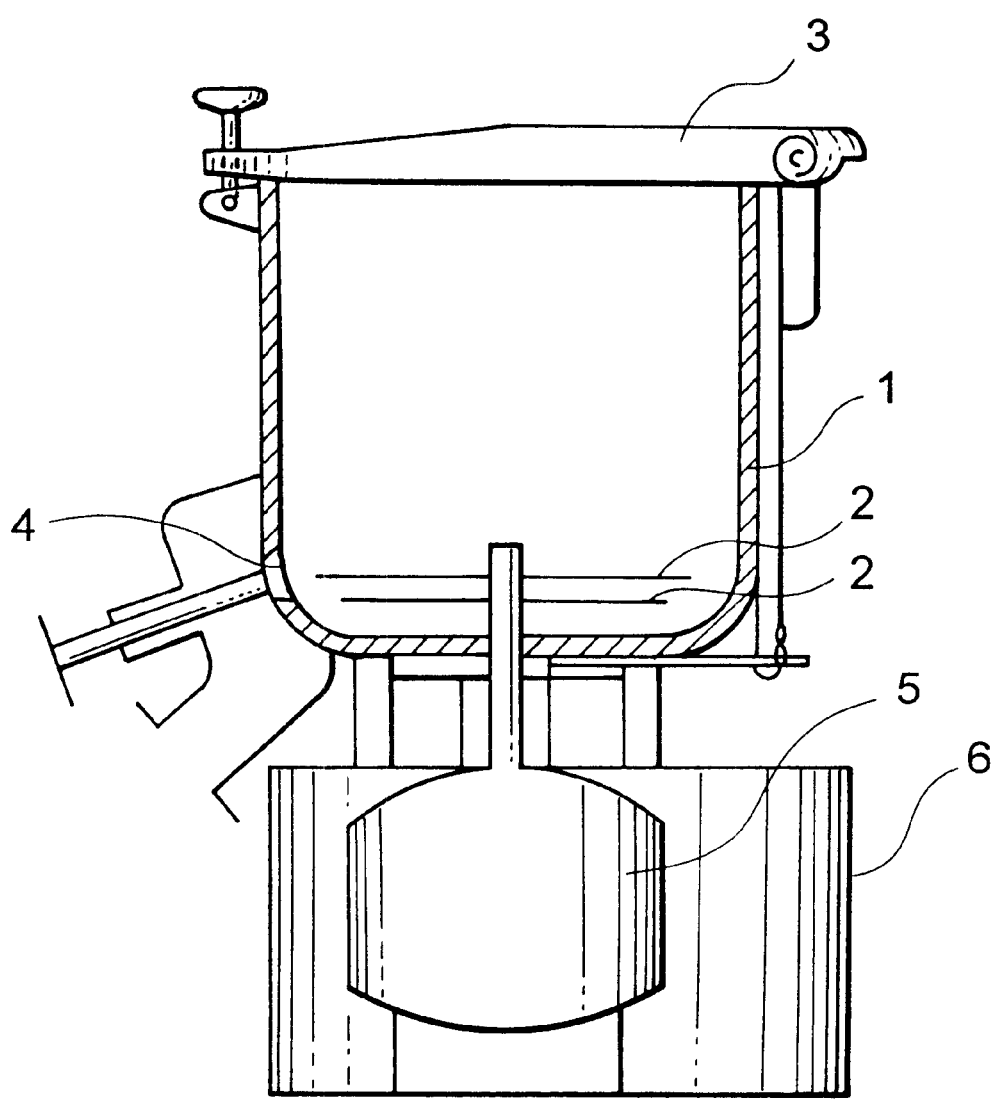
FIG. 2 is a cross-section showing diagrammatically a Henshel-type mixer that is a high-speed blade mixer in the manufacturing process of the algae cultivating medium as set forth in Embodiment 1.
Figure 3:
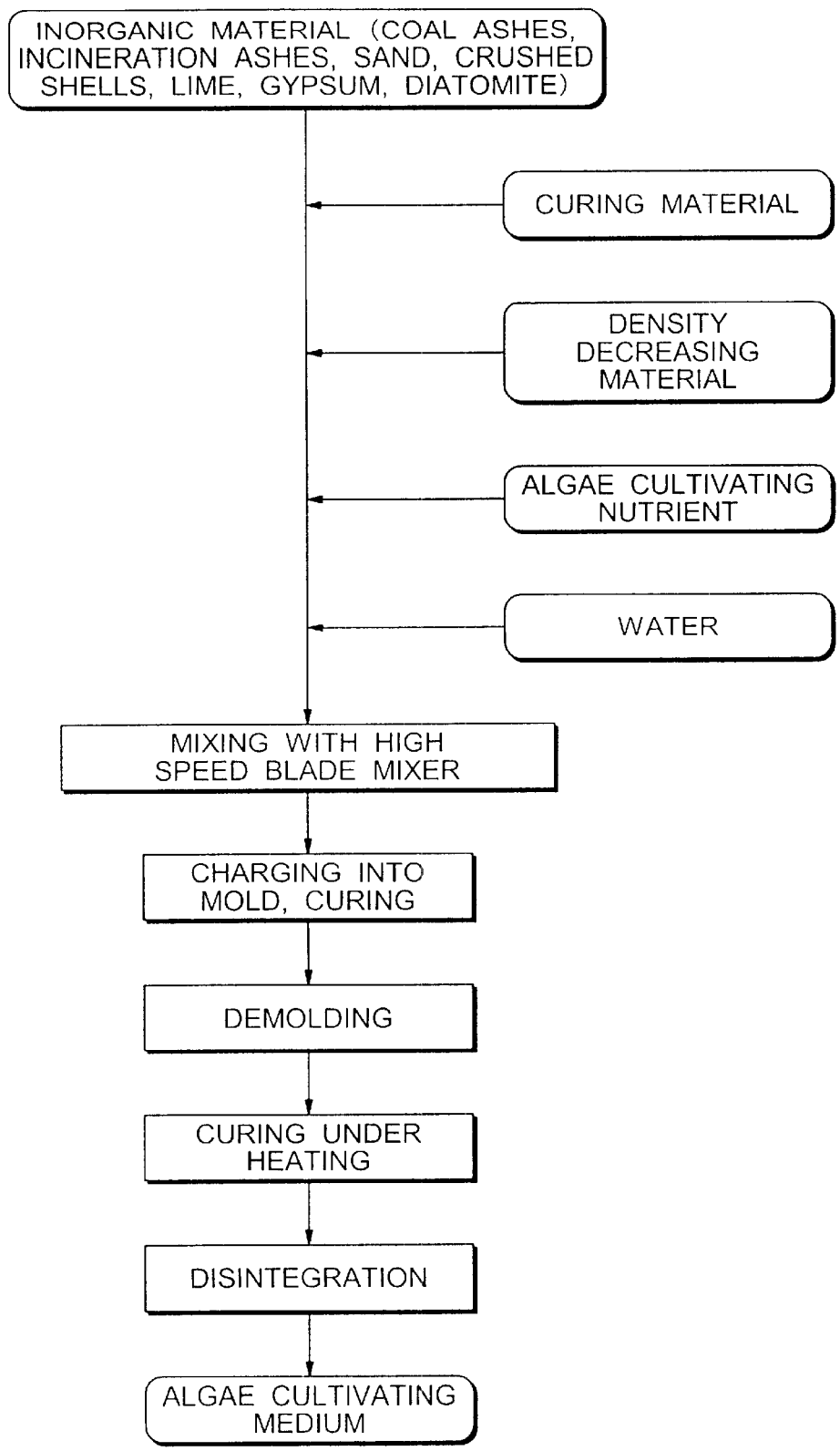
FIG. 3 is a flow-chart of a manufacturing process of an algae cultivating medium according to a disintegrating molding method as set forth in Embodiment 2 in which inorganic material is primary raw material.

To any one inorganic material of coal ashes, incineration ashes, sands and crushed shells, a curing material and density decreasing material and algae cultivating nutriment were added, followed by further addition of water. The mixing was carried out ussing a Henshel-type mixer which is a kind of a high-speed blade mixer having agitating blades in order to have a mixing in a large quantity in a short time. FIG. 2 is a cross-section showing diagrammatically the Henshel-type mixer. In FIG. 2, reference numeral 1 denotes a mixing tank, reference numeral 2 denotes a agitation blade, reference numeral 3 denotes a cap portion of the tank, reference numeral 4 denotes an exhausting outlet and reference numeral 6 denotes a table.

The mixture obtained by the Henshel-type mixer was charged to molds to form molded bodies and cured (keeping temperature and humidity). Subsequently, the molded bodies were cured further by heating up to 110° C. for 24 hours and then pellets of the algae cultivating media were manufactured. In the case when the manufactured molded body contains much alkali component showing high pH value, the molded body is immersed in water to lower the pH thereof as necessity arises. The inorganic material used was subjected to a treatment for eliminating a component that pollutes environment such as heavy metals and poisonous organic materials and dried.

Table 1 shows conditions and results of runs carrying out in this Embodiment 1. The runs of manufacturing the molded bodies of the algae cultivating media shown in Table 1, coal ashes, incineration ashes, sands and crushed shells were used as inorganic material, sodium silicate as the curing material, pearlite as the density decreasing material, and sodium phosphate and iron phosphate and sodium nitrate in the ratio of 5:1:5 as the algae cultivating nutriment.

These molded bodies were tested in a water tank that was filled with seawater containing algae. We used sodium silicate as the curing material and pearlite as the density decreasing material for all inorganic materials in the runs as seen in Table 1. Thereby, it was confirmed that the molded bodies had the densities of 1 g/cm³ or less and could float on water, and the algae could grow and increase.

TABLE 1

| | Algae Cultivating Media by Standard Molding | | | | | | |
|---|---|---|---|---|---|---|---|
| | Run No. | | | | | | |
| Molding method | 1-1 | 1-2 | 1-3 | 1-4 | 1-5 | 1-6 | Note |
| | | | Standard molding | | | | |
| Coal ashes | 100 | 0 | 0 | 0 | 100 | 100 | Inorganic material |
| Incineration ashes | 0 | 100 | 0 | 0 | 0 | 0 | Inorganic material |
| Sands | 0 | 0 | 100 | 0 | 0 | 0 | Inorganic material |
| Crushed shells | 0 | 0 | 0 | 100 | 0 | 0 | Inorganic material |
| Curing material | 5 | 5 | 5 | 5 | 20 | 20 | Sodium silicate |
| Density decreasing material | 30 | 30 | 30 | 30 | 30 | 30 | Pearlite |

TABLE 1-continued

Algae Cultivating Media by Standard Molding

| Molding method | Run No. 1-1 | 1-2 | 1-3 | 1-4 Standard molding | 1-5 | 1-6 | Note |
|---|---|---|---|---|---|---|---|
| Nutriment of algae cultivating | 11 | 11 | 11 | 11 | 11 | 11 | Sodium phosphate + iron phosphate + sodium nitrate |
| Density | 0.9 | 0.9 | 0.9 | 0.9 | 0.9 | 0.9 | Unit: g/cm$^3$ |
| Floatation on water | Floating | Floating | Floating | Floating | Floating | Floating | |
| Increase of algae | Increased | Increased | Increased | Increased | Increased | Not increased | Carried out in a water tank |

Note:
The material ratio found in the table is expressed in weight ratio.
1-1 to 1-5: Immersed in water after molding into pellet (pH is about 8).
1-6: Not immersed in water after molding into pellet (pH is about 11).

Embodiment 2

A disintegrating molding process shown in FIG. 2 was applied for manufacturing molded bodies of algae cultivating media in Embodiment 2. The conditions of the runs in this embodiment were adjusted to be identical with the conditions for Embodiment 1. The inorganic material added with the curing material, the density decreasing material and the algae cultivating nutriment, and further added with water were mixed using Henshel-type mixer.

The mixture obtained at each run was charged to large size molds to obtain molded bodies having square face with 300 mm sides and 30 mm thickness. The molded bodies were put into a disintegrating granulation machine to obtain angular molded bodies having average diameter of about 5 mm. Tests identical with the ones for Embodiment 1 were carried out for molded bodies manufactured at the runs of Embodiment 2. The results are shown in Table 2.

TABLE 2

Algae Cultivating Media due to Disintegration Molding

| Molding method | Run No. 2-1 | 2-2 | 2-3 Disintegration molding | 2-4 | 2-5 | 2-6 | Note |
|---|---|---|---|---|---|---|---|
| Coal ashes | 100 | 0 | 0 | 0 | 100 | 100 | Inorganic material |
| Incineration ashes | 0 | 100 | 0 | 0 | 0 | 0 | Inorganic material |
| Sands | 0 | 0 | 100 | 0 | 0 | 0 | Inorganic material |
| Crushed shells | 0 | 0 | 0 | 100 | 0 | 0 | Inorganic material |
| Curing material | 5 | 5 | 5 | 5 | 20 | 20 | Sodium silicate |
| Density decreasing material | 30 | 30 | 30 | 30 | 30 | 30 | Pearlite |
| Algae cultivating nutriment | 11 | 11 | 11 | 11 | 11 | 11 | Sodium phosphate + iron phosphate + sodium nitrate |
| Density | 0.9 | 0.9 | 0.9 | 0.9 | 0.9 | 0.9 | Unit: g/cm$^3$ |
| Floatation on water | Floating | Floating | Floating | Floating | Floating | Floating | |
| Increase of algae | Increased | Increased | Increased | Increased | Increased | Not increased | Carried out in a water tank |

Note:
The material ratio found in the table is expressed in weight ratio.
2-1 to 2-5: Immersed in water after molding into pellet (pH is about 8).
2-6: Not immersed in water after molding into pellet (pH is about 11).

As seen from table 2, the molded bodies manufactured by the disintegration molding method, similar to the ones by standard molding method, were floatable on water having densities of 1 g/cm$^3$ or less and could grow increase the algae. From these results, it is found that the disintegration molding method is advantageous for manufacturing a large quantity of the molded body since the number of operation for charging the mixture into the mold in standard method can be greatly decreased.

Embodiment 3

Figure 4:
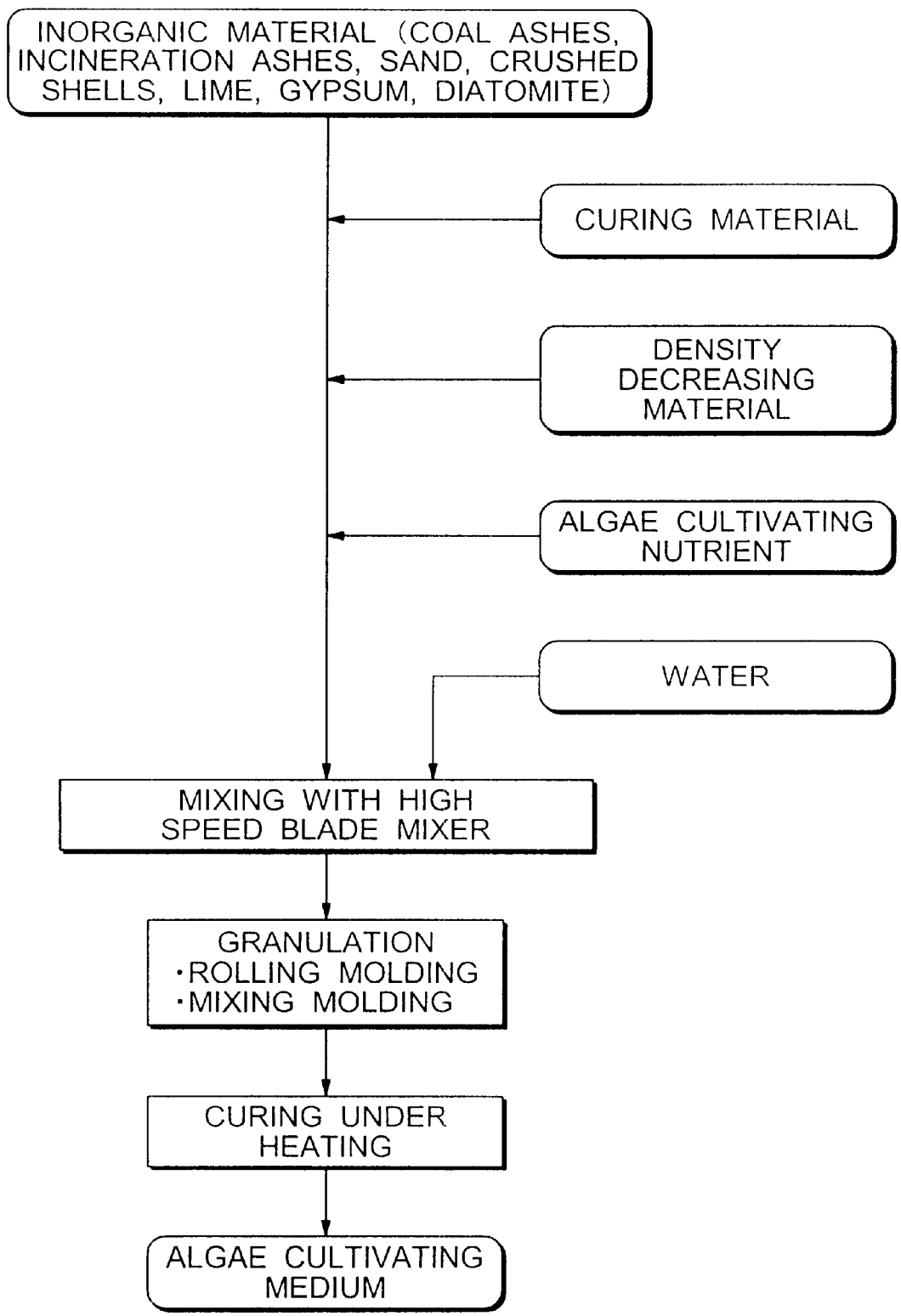
FIG. 4 is a flow-chart of a molding process of an algae cultivating medium according to an agitating/mixing molding method disclosed in Embodiment 3 in which inorganic material is primary raw material.

A process of agitation molding of algae cultivating media as shown in FIG. 4 was carried out at this embodiment. The conditions of the runs in this embodiment were adjusted to be identical with the conditions for Embodiment 1. The inorganic material added with the curing material, the density decreasing material and the algae cultivating nutriment, and further added with water were mixed using Henshel-type mixer.

The mixture after mixing was agitated by the rotating blade thereof to carry out agitation molding. The agitation molding can be divided into rolling molding and mixing molding by the speed of agitation of the rotating blade. In the rolling molding, water was poured in the mixture of powder material while rotating the rotating blade of the mixer with a low speed. Thereby, spherical molded bodies having diameters of approximately 5 to 15 mm were formed. On the other hand, in the mixing molding method, the rotating blades of the mixer were rotated with a high speed to cause a turbulent flow of the mixture of powder material. Into this turbulent flow of the powder mixture, water was jetted out with a spray to obtain spherical molded bodies of a diameter of approximately 5 to 19 mm. By supplying vapor to a jacket of the mixer, curing under heating (110° C., 24 hours) was carried out to manufacture an algae cultivating media.

When the manufactured molded bodies contains much of alkali components to be high in its pH, as necessity arises, the molded bodies are immersed in water to lower the pH thereof identically with the case for Embodiment 1. The results are shown in Table 3.

As seen from the results of Table 3, the molded bodies manufactured by the mixing molding method were floatable in water having density of 1 g/cm$^3$ or less and could grow and increase the algae similar to the case in which the curing is carried out at the condition for the standard molding method. This agitation molding method was found to be able to manufacture large quantity of the algae cultivating media as spherical molded bodies. The manufacturing quantity can be adjusted to demands by choosing the size of the mixer. Further, the present Embodiment obviously showed that mixing, molding and curing at an elevated temperature could be carried out in a same mixer. Of course, manufacturing of molded bodies by the rolling molding method using a drum-type or pan-type granulation machine can be applied exclusively for the molding process. Also the mixing molding method using so-called a flexo-mix machine for example, for performing each process separately.

Embodiment 4

Figure 5:
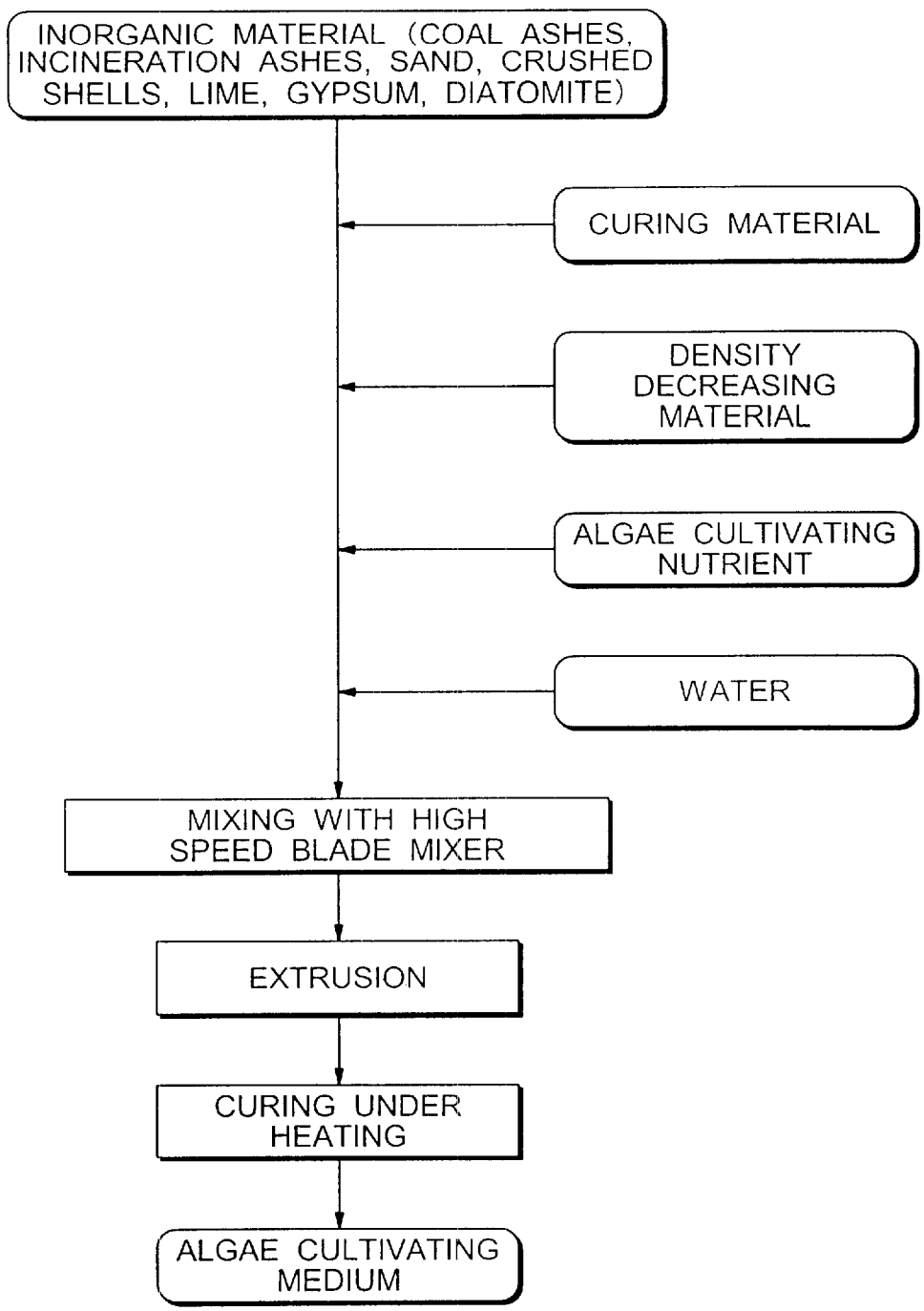
FIG. 5 is a flow-chart of a manufacturing process of an algae cultivating medium according to an extrusion molding method disclosed in Embodiment 4 in which inorganic material is primary raw material.

An extrusion molding process for the algae cultivating media carried out in Embodiment 4 is shown in FIG. 5. The inorganic material added with the curing material, the density decreasing material and the algae cultivating nutriment, and further added with water were mixed using Henshel-type mixer. Thus obtained mixture was supplied to a screw granulation machine to prepare cylindrical molded bodies having a diameter of approximately 10 mm and a length of approximately 10 mm. The molded bodies were cured at an elevated temperature (110° C., 24 hours) to obtain algae cultivating media. The results are shown in Table 4.

TABLE 3

Algae Cultivating Media due to Rolling Molding and Mixing Molding

| Molding method | 3-1 | 3-2 | 3-3 | 3-4 | 3-5 | 3-6 | 3-7 | 3-8 | 3-9 | 3-10 | 3-11 | 3-12 | Note |
|---|---|---|---|---|---|---|---|---|---|---|---|---|---|
| | | | Rolling molding | | | | | | Mixing molding | | | | |
| Coal ashes | 100 | 0 | 0 | 0 | 100 | 100 | 100 | 0 | 0 | 0 | 100 | 100 | Inorganic material |
| Incineration ashes | 0 | 100 | 0 | 0 | 0 | 0 | 0 | 100 | 0 | 0 | 0 | 0 | Inorganic material |
| Sands | 0 | 0 | 100 | 0 | 0 | 0 | 0 | 0 | 100 | 0 | 0 | 0 | Inorganic material |
| Crushed shells | 0 | 0 | 0 | 100 | 0 | 0 | 0 | 0 | 0 | 100 | 0 | 0 | Inorganic material |
| Curing material | 5 | 5 | 5 | 5 | 20 | 20 | 5 | 5 | 5 | 5 | 20 | 20 | Sodium silicate |
| Density decreasing material | 30 | 30 | 30 | 30 | 30 | 30 | 30 | 30 | 30 | 30 | 30 | 30 | Pearlite |
| Algae cultivating nutriment | 11 | 11 | 11 | 11 | 11 | 11 | 11 | 11 | 11 | 11 | 11 | 11 | Sodium phosphate + iron phosphate + sodium nitrate |
| Density | 0.9 | 0.9 | 0.9 | 0.9 | 0.9 | 0.9 | 0.9 | 0.9 | 0.9 | 0.9 | 0.9 | 0.9 | Unit: g/cm$^3$ |
| Floatation on water | Floating | Floating | Floating | Floating | Floating | Floating | Floating | Floating | Floating | Floating | Floating | Floating | |
| Increase of algae | Increased | Increased | Increased | Increased | Increased | Not increased | Increased | Increased | Increased | Increased | Increased | Not increased | carried out in a water tank |

Note:
The material ratio found in the table is expressed in weight ratio.
3-1 to 3-5, 3-7 to 3-11: Immersed in water after molding into pellet (pH is about 8).
3-6: and 3-12: Not immersed in water after molding into pellet (pH is about 11).

TABLE 4

Algae Cultivating Media due to Extrusion Molding

| | Run No. | | | | | | |
|---|---|---|---|---|---|---|---|
| Molding method | 4-1 | 4-2 | 4-3 | 4-4 | 4-5 | 4-6 | Note |
| | | | Extrusion molding | | | | |
| Coal ashes | 100 | 0 | 0 | 0 | 100 | 100 | Inorganic material |
| Incineration ashes | 0 | 100 | 0 | 0 | 0 | 0 | Inorganic material |
| Sands | 0 | 0 | 100 | 0 | 0 | 0 | Inorganic material |
| Crushed shells | 0 | 0 | 0 | 100 | 0 | 0 | Inorganic material |
| Curing material | 5 | 5 | 5 | 5 | 20 | 20 | Sodium silicate |
| Density decreasing material | 30 | 30 | 30 | 30 | 30 | 30 | Pearlite |
| Algae cultivating nutriment | 11 | 11 | 11 | 11 | 11 | 11 | Sodium phosphate + iron phosphate + sodium nitrate |
| Density | 0.9 | 0.9 | 0.9 | 0.9 | 0.9 | 0.9 | Unit: g/cm$^3$ |
| Floatation on water | Floating | Floating | Floating | Floating | Floating | Floating | |
| Increase of algae | Increased | Increased | Increased | Increased | Increased | Not increased | Carried out in a water tank |

Note:
The material ratio found in the table is expressed in weight ratio.
4-1 to 4-5: Immersed in water after molding into pellet (pH is about 8).
4-6: Not immersed in water after molding into pellet (pH is about 11).

The molded bodies prepared were immersed in water identically with Embodiment 1 to lower pH values when the bodies contained much alkaline component showing high pH values thereof, as necessity arises.

As seen from the results of Table 4, the molded bodies prepared by extrusion molding by the extrusion molding method were floatable in water having density of 1 g/cm$^3$ or less and could grow and increase the algae similar to the case in which the molding and curing were carried out at the condition of the standard molding method.

Embodiment 5

Figure 6:
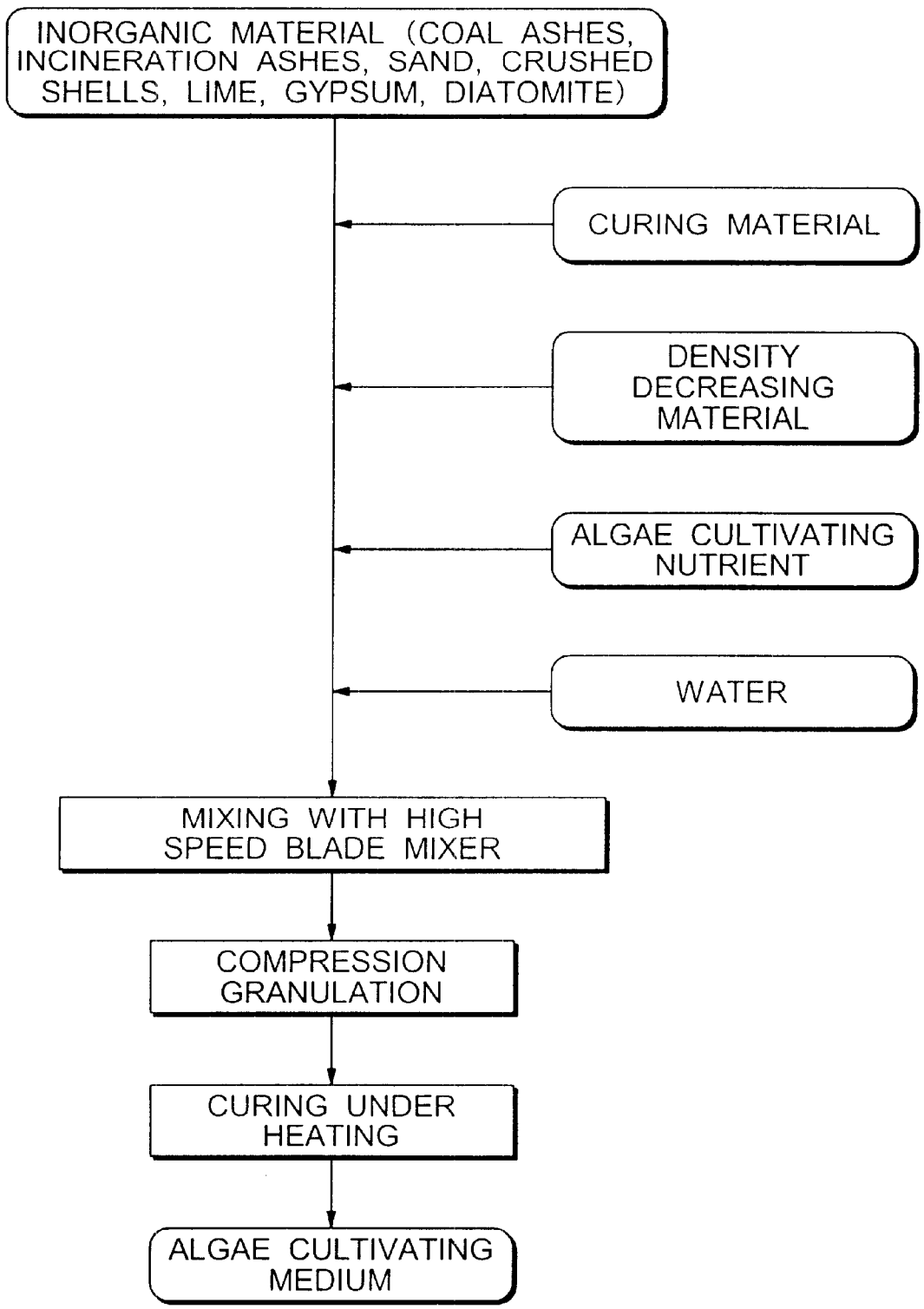
FIG. 6 is a diagram showing a manufacturing process of an algae cultivating medium according to a compression molding method disclosed in Embodiment 5 in which inorganic material is primary raw material.

FIG. 6 shows a process of compression molding of algae cultivating media carried out at Embodiment 5. The conditions of the runs in this embodiment were adjusted to be identical with the conditions for Embodiment 1. The inorganic material added with the curing material, the density decreasing material and the algae cultivating nutriment, and further added with water were mixed using Henshel-type mixer. Thus obtained mixture was supplied to a hydraulic compression granulation machine to prepare cylindrical molded bodies having about 10 mm in diameter and about 10 mm in length. The molded bodies were cured at an elevated temperature (110° C., 24 hours) to obtain algae cultivating media.

The molded bodies prepared immersed in water identically with Embodiment 1 to lower pH values when the bodies contained much alkaline component showing high pH values thereof,

TABLE 5

Algae Cultivating Media due to Compression Molding

| | Run No. | | | | | | |
|---|---|---|---|---|---|---|---|
| Molding method | 5-1 | 5-2 | 5-3 | 5-4 | 5-5 | 5-6 | Note |
| | | | Compression | | | | |
| Coal ashes | 100 | 0 | 0 | 0 | 100 | 100 | Inorganic material |
| Incineration ashes | 0 | 100 | 0 | 0 | 0 | 0 | Inorganic material |
| Sands | 0 | 0 | 100 | 0 | 0 | 0 | Inorganic material |
| Crushed material | 0 | 0 | 0 | 100 | 0 | 0 | Inorganic material |
| Curing material | 5 | 5 | 5 | 5 | 20 | 20 | Sodium silicate |
| Density decreasing material | 30 | 30 | 30 | 30 | 30 | 30 | Pearlite |

TABLE 5-continued

Algae Cultivating Media due to Compression Molding

| | \multicolumn{6}{c|}{Run No.} | |
|---|---|---|---|---|---|---|---|
| Molding method | 5-1 | 5-2 | 5-3 | 5-4 | 5-5 | 5-6 | Note |
| | | | \multicolumn{2}{c}{Compression} | | | |
| Algae cultivating nutriment | 11 | 11 | 11 | 11 | 11 | 11 | Sodium phosphate + iron phosphate + sodium nitrate |
| Density | 0.9 | 0.9 | 0.9 | 0.9 | 0.9 | 0.9 | Unit: g/cm³ |
| Floatation on water | Floating | Floating | Floating | Floating | Floating | Floating | |
| Increase of algae | Increased | Increased | Increased | Increased | Increased | Not increased | Carried out in a water tank |

Note:
The material ratio found in the table is expressed in weight ratio.
5-1 to 5-5: Immersed in water after molding into pellet (pH is about 8).
5-6: Not immersed in water after molding into pellet (pH is about 11).

as necessity arises.

The results are shown in Table 5.

As seen from the results of Table 4, the molded bodies prepared by the extrusion molding method were floatable in water having density of 1 g/cm³ or less and could grow and increase the algae similar to the case in which the molding and curing were carried out at the condition of the standard molding method.

Embodiment 6

Manufacturing and testing runs were carried out at similar conditions to the aforementioned embodiments except for restricting the inorganic material as coal ashes and varying the kinds of the curing material. The results are shown in Table 6.

TABLE 6

Effect of various kinds of curing material

| | \multicolumn{8}{c|}{Run No.} | |
|---|---|---|---|---|---|---|---|---|---|
| Molding method | 6-1 | 6-2 | 6-3 | 6-4 | 6-5 | 6-6 Disintegration molding | 6-7 Rolling molding | 6-8 Mixing molding | Note |
| | \multicolumn{5}{c}{Standard molding} | | | | |
| Coal ashes | 100 | 100 | 100 | 100 | 100 | 100 | 100 | 100 | Inorganic material |
| Cement | 20 | 0 | 0 | 0 | 10 | 0 | 0 | 0 | Curing material |
| Sodium silicate | 0 | 5 | 0 | 0 | 0 | 5 | 5 | 5 | Curing material |
| Potassium silicate | 0 | 0 | 5 | 0 | 0 | 0 | 0 | 0 | Curing material |
| Silica sol | 0 | 0 | 0 | 0 | 10 | 0 | 0 | 0 | Curing material |
| Pearlite | 30 | 30 | 30 | 30 | 30 | 30 | 30 | 30 | Density decreasing material |
| Algae cultivating nutriment | 11 | 11 | 11 | 11 | 11 | 11 | 11 | 11 | Note 2 |
| Density | 0.95 | 0.9 | 0.9 | 0.9 | 0.95 | 0.9 | 0.9 | 0.9 | Unit: g/cm³ |
| Floatation on water | Floating | Floating | Floating | Floating | Floating | Floating | Floating | Floating | |

| | \multicolumn{7}{c|}{Run No.} | | |
|---|---|---|---|---|---|---|---|---|---|
| Molding method | 6-9 Extrusion molding | 6-10 Compression molding | 6-11 Disintegration molding | 6-12 Rolling molding | 6-13 Mixing molding | 6-14 Extrusion molding | 6-15 Compression molding | Reference Standard molding | Note |
| Coal ashes | 100 | 100 | 100 | 100 | 100 | 100 | 100 | 100 | Inorganic material |
| Cement | 0 | 0 | 20 | 20 | 20 | 20 | 20 | 0 | Curing material |

TABLE 6-continued

Effect of various kinds of curing material

| Sodium silicate | 5 | 5 | 0 | 0 | 0 | 0 | 0 | 0 | Curing material |
|---|---|---|---|---|---|---|---|---|---|
| Potassium silicate | 0 | 0 | 0 | 0 | 0 | 0 | 0 | 0 | Curing material |
| Lithium silicate | 0 | 0 | 0 | 0 | 0 | 0 | 0 | 0 | Curing material |
| Silica sol | 0 | 0 | 0 | 0 | 0 | 0 | 0 | 0 | Curing material |
| Pearlite | 30 | 30 | 30 | 30 | 30 | 30 | 30 | 30 | Density decreasing material |
| Algae cultivating nutriment | 11 | 11 | 11 | 11 | 11 | 11 | 11 | 11 | Note 2 |
| Density | 0.9 | 0.9 | 0.95 | 0.95 | 0.95 | 0.95 | 0.95 | Powder | Unit: g/cm$^3$ |
| Floatation on water | Floating | Floating | Floating | Floating | Floating | Floating | Floating | — | |

Note 1: The unit of the compounding ratio in the table is weight ratio.
Note 2: Iron phosphate/sodium phosphate/sodium nitrate = 1/5/5.

As obvious from Table 6, it is confirmed that the molded bodies can float on water and grow and increase algae as cultivating media even when we use sodium silicate, potassium silicate, lithium silicate and silica sol other than cement as curing material.

Further, test runs for finding the effect of the difference in the molding methods were carried out restricting the curing material to sodium silicate that was identical with the cases for Embodiments 2 to 5. The test run showed that the molded bodies had the densities of 1 g/cm$^3$ or less and were floatable on water and can grow and increase algae. The results were almost the same with those of the standard molding process.

From these results it is confirmed that all the molding process tested including disintegration molding, agitation molding (rolling molding, mixing molding), extrusion molding and compression molding can be available for manufacturing algae as cultivating media obtaining almost identical results with the cases for the standard molding process.

Embodiment 7

Phosphate compounds effective as algae cultivating nutriment were used as curing materials. In addition, iron phosphate or iron oxyhydroxide (Fe component) and sodium nitrate (N component) are used as other algae cultivating nutriments to manufacture the molded bodies of the algae cultivating media. The results are shown in Table 7.

TABLE 7

Effect of curing materials that are algae cultivating nutriment

| | Run No. | | | | | | | | |
|---|---|---|---|---|---|---|---|---|---|
| Molding method | 7-1 | 7-2 | 7-3 | 7-4 | 7-5 | 7-6 Disintegration molding | 7-7 Rolling molding | 7-8 Mixing molding | Note |
| | Standard molding | | | | | | | | |
| Sodium phosphate | 15 | 0 | 0 | 0 | 15 | 15 | 15 | 15 | Curing material |
| Sodium dihydrogen phosphate | 0 | 15 | 0 | 0 | 0 | 0 | 0 | 0 | Curing material |
| Aluminum phosphate | 0 | 0 | 15 | 0 | 0 | 0 | 0 | 0 | Curing material |
| Aluminum hydrogen phosphate | 0 | 0 | 0 | 15 | 0 | 0 | 0 | 0 | Curing material |
| Pearlite | 30 | 30 | 30 | 30 | 30 | 30 | 30 | 30 | Density decreasing material |
| Iron phosphate | 5 | 5 | 5 | 5 | 5 | 5 | 5 | 5 | Algae cultivating nutriment |

TABLE 7-continued

Effect of curing materials that are algae cultivating nutriment

| Density | 0.85 | 0.85 | 0.9 | 0.9 | 0.85 | 0.85 | 0.85 | 0.85 | Unit: g/cm³ |
|---|---|---|---|---|---|---|---|---|---|
| Floatation on water | Floating | Floating | Floating | Floating | Floating | Floating | Floating | Floating | |
| Increase of algae | Increased | Increased | Increased | Increased | Increased | Increased | Increased | Increased | Carried out in a water tank |

| | Run No. | | | | | | | |
|---|---|---|---|---|---|---|---|---|
| | 7-9 | 7-10 | 7-11 | 7-12 | 7-13 | 7-14 | 7-15 | |
| Molding method | Extrusion molding | Compression molding | Disintegration molding | Rolling molding | Mixing molding | Extrusion molding | Compression molding | Note |
| Sodium phosphate | 15 | 15 | 0 | 0 | 0 | 0 | 0 | Curing material |
| Sodium dihydrogen phosphate | 0 | 0 | 0 | 0 | 0 | 0 | 0 | Curing material |
| Aluminum phosphate | 0 | 0 | 15 | 15 | 15 | 15 | 15 | Curing material |
| Aluminum hydrogen phosphate | 0 | 0 | 0 | 0 | 0 | 0 | 0 | Curing material |
| Pearlite | 30 | 30 | 30 | 30 | 30 | 30 | 30 | Density decreasing material |
| Iron phosphate | 5 | 5 | 5 | 5 | 5 | 5 | 5 | Algae cultivating nutriment |
| Density | 0.85 | 0.85 | 0.9 | 0.9 | 0.9 | 0.9 | 0.9 | Unit: g/cm³ |
| Floatation on water | Floating | Floating | Floating | Floating | Floating | Floating | Floating | |
| Increase of algae | Increased | Increased | Increased | Increased | Increased | Increased | Increased | Carried out in a water tank |

Note 1: The unit of the compounding ratio in the table is weight ratio.

As obvious from the results, we can find that all of sodium phosphate, sodium dihydrogen phosphate, aluminum phosphate and aluminum hydrogen phosphate are effective as the curing material in the standard molding method. It is confirmed that the molded bodies, which can float on water and multiply the algae, can be obtained by using these as the curing material.

In addition, the tests were carried out under the identical conditions with Embodiments 2 to 5 under the condition where sodium phosphate and aluminum phosphate was added as a phosphate compounds. Thereby, the influence of the difference in the molding steps was examined. From the test results, it was confirmed that the obtained molded bodies were almost identical with the cases for the standard molding process in which the molded bodies had the densities of 1 g/cm³ or less, and could float on water and can grow and increase algae. From the present results, it is confirmed that the phosphate compounds effective as the algae cultivating nutriment are applicable as the curing material in any molding method of the inorganic materials of the present invention, that is, in all of standard molding method, disintegration molding method, agitating molding method (rolling molding method, mixing molding method), extrusion molding method and compression molding method.

Figure 7:
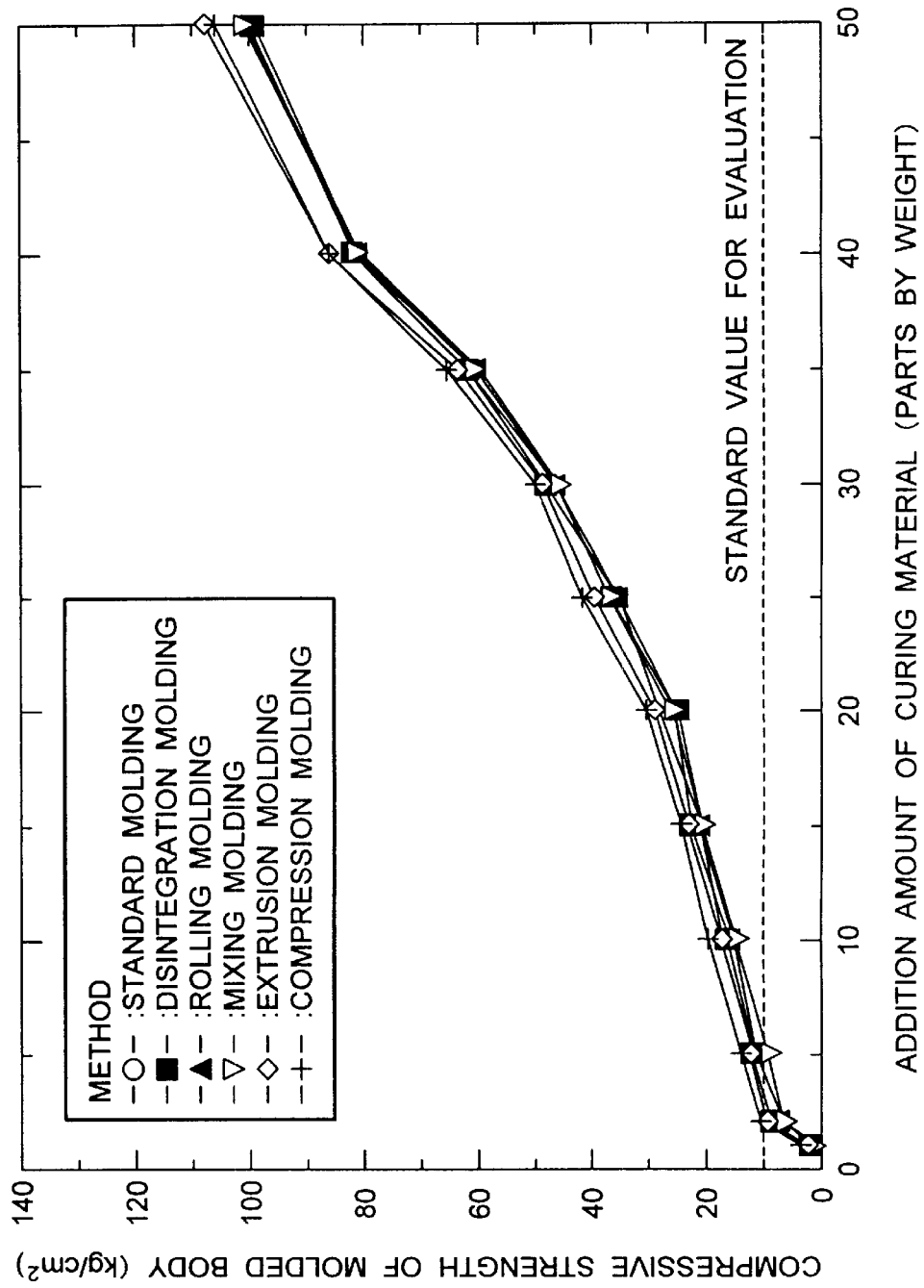
FIG. 7 is a diagram showing the relationship between an addition amount of a curing material in the algae cultivating medium according to a standard molding method as set forth in Embodiment 7 and the strength of the algae cultivating medium.

Under the conditions of the 6-1, 6-2 runs of Embodiment 6 and the 7-1 run of Embodiment 7, addition amount of the respective curing materials was varied for molded bodies manufactured. Then compressive strength of the manufactured molded bodies was measured. The result was shown in FIG. 7. From this result, the strength satisfy the standard strength value at 5 parts by weight or more of the curing material relative to 100 parts by weight of inorganic material.

Figure 8:
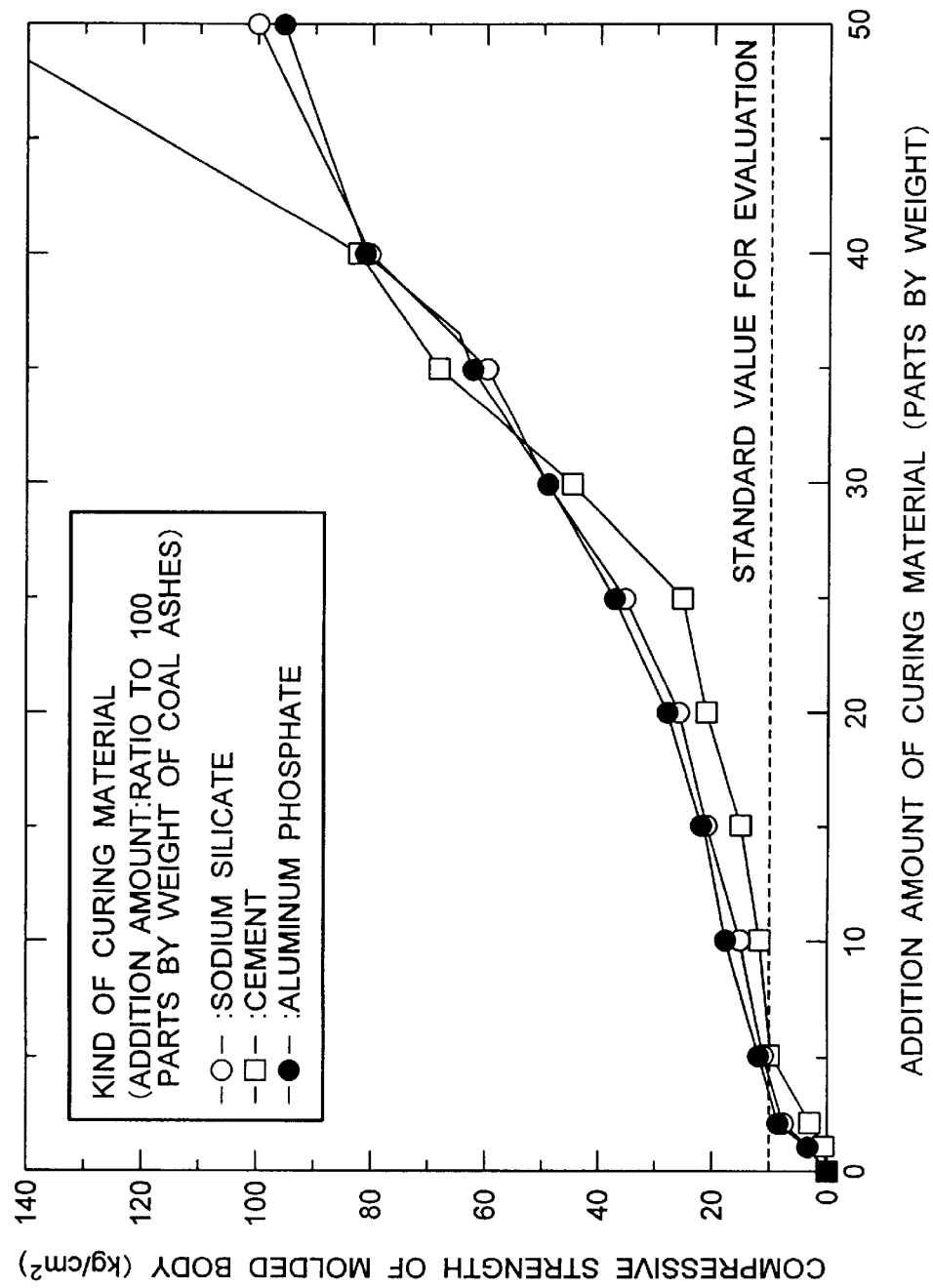
FIG. 8 is a diagram showing the relationship between an addition amount of the curing material due to the standard molding method as set forth in Embodiment 7 and the strength of the algae cultivating medium.

Further, the effect of the difference of the molding method at the molding step upon the strength was examined keeping the curing material fixed to sodium silicate. The result is shown in FIG. 8. From this result, we can find that the difference of the molding step does not influence on the strength, and all the molding methods examined satisfy the standard strength value at 5 parts by weight or more of the curing material.

Embodiment 8

The algae cultivating nutriment were varied in its kinds in which the inorganic material was restricted to coal ashes and the curing material was restricted to sodium silicate. The algae cultivating media were prepared obeying the standard molding conditions described at Embodiment 1 except for the variation described above. The obtained algae cultivating media were evaluated by the method described at Embodiment 1. The results are shown in Table 8.

TABLE 8

Results of application of various kinds of algae cultivating nutriments

| Molding method | Run No. 8-1 | 8-2 | 8-3 | 8-4 | 8-5 | 8-6 Disintegration molding | 8-7 Rolling molding | 8-8 Mixing molding | 8-9 Extrusion molding | 8-10 Compression molding | Reference Standard molding | Note |
|---|---|---|---|---|---|---|---|---|---|---|---|---|
| | Standard molding | | | | | | | | | | | |
| Coal ashes | 100 | 100 | 100 | 100 | 100 | 100 | 100 | 100 | 100 | 100 | 100 | Inorganic material |
| Sodium silicate | 5 | 5 | 5 | 5 | 5 | 5 | 5 | 5 | 5 | 5 | 5 | Curing material |
| Pearlite | 30 | 30 | 30 | 30 | 30 | 30 | 30 | 30 | 30 | 30 | 30 | Density decreasing material |
| Iron phosphate | 1 | 0 | 1 | 0 | 0.5 | 0.5 | 0.5 | 0.5 | 0.5 | 0.5 | 0 | Algae cultivating nutriment |
| Iron oxyhydroxide | 0 | 1 | 0 | 1 | 0.5 | 0.5 | 0.5 | 0.5 | 0.5 | 0.5 | 0 | Algae cultivating nutriment |
| Aluminum phosphate | 0 | 0 | 5 | 5 | 2.5 | 2.5 | 2.5 | 2.5 | 2.5 | 2.5 | 0 | Algae cultivating nutriment |
| Sodium phosphate | 5 | 5 | 0 | 0 | 2.5 | 2.5 | 2.5 | 2.5 | 2.5 | 2.5 | 0 | Algae cultivating nutriment |
| Sodium nitrate | 5 | 5 | 5 | 5 | 5 | 5 | 5 | 5 | 5 | 5 | 0 | Algae cultivating nutriment |
| Density | 0.9 | 0.9 | 0.9 | 0.9 | 0.9 | 0.9 | 0.9 | 0.9 | 0.9 | 0.9 | 0.85 | Unit: g/cm$^3$ |
| Floatation on water | Floating | Floating | Floating | Floating | Floating | Floating | Floating | Floating | Floating | Floating | Floating | |
| Increase of algae | Increased | Increased | Increased | Increased | Increased | Increased | Increased | Increased | Increased | Increased | Not Increased | Carried out in a water tank |

Note:
The unit of the compounding ratio in the table is weight ratio.

As seen from Table 8, the algae cultivating media could float in water and could obtain increase of the algae when iron phosphate, iron oxyhydroxide, aluminum phosphate, and sodium phosphate were used as the algae cultivating nutriment.

In addition, the effect of the difference of the molding methods upon the molded body strength for the case when the algae cultivating nutriments were added in combination for iron phosphate and iron oxyhydroxide (Fe content), aluminum phosphate and sodium phosphate (P content), and sodium nitrate (n content). The tests were carried out with the methods identical with the aforementioned Embodiments 2 to 5. The obtained results are shown together in Table 8. As obvious from these results, all of the obtained molded bodies were approximately identical with the cases where the standard molding method was applied. It is confirmed that the molded bodies have the densities of 1 g/cm$^3$ or less and can float on water and can grow and increase the algae. From these results it is confirmed that the adding the algae cultivating nutriment is effective and adequate without regard to the difference of the molding methods.

Figure 9:
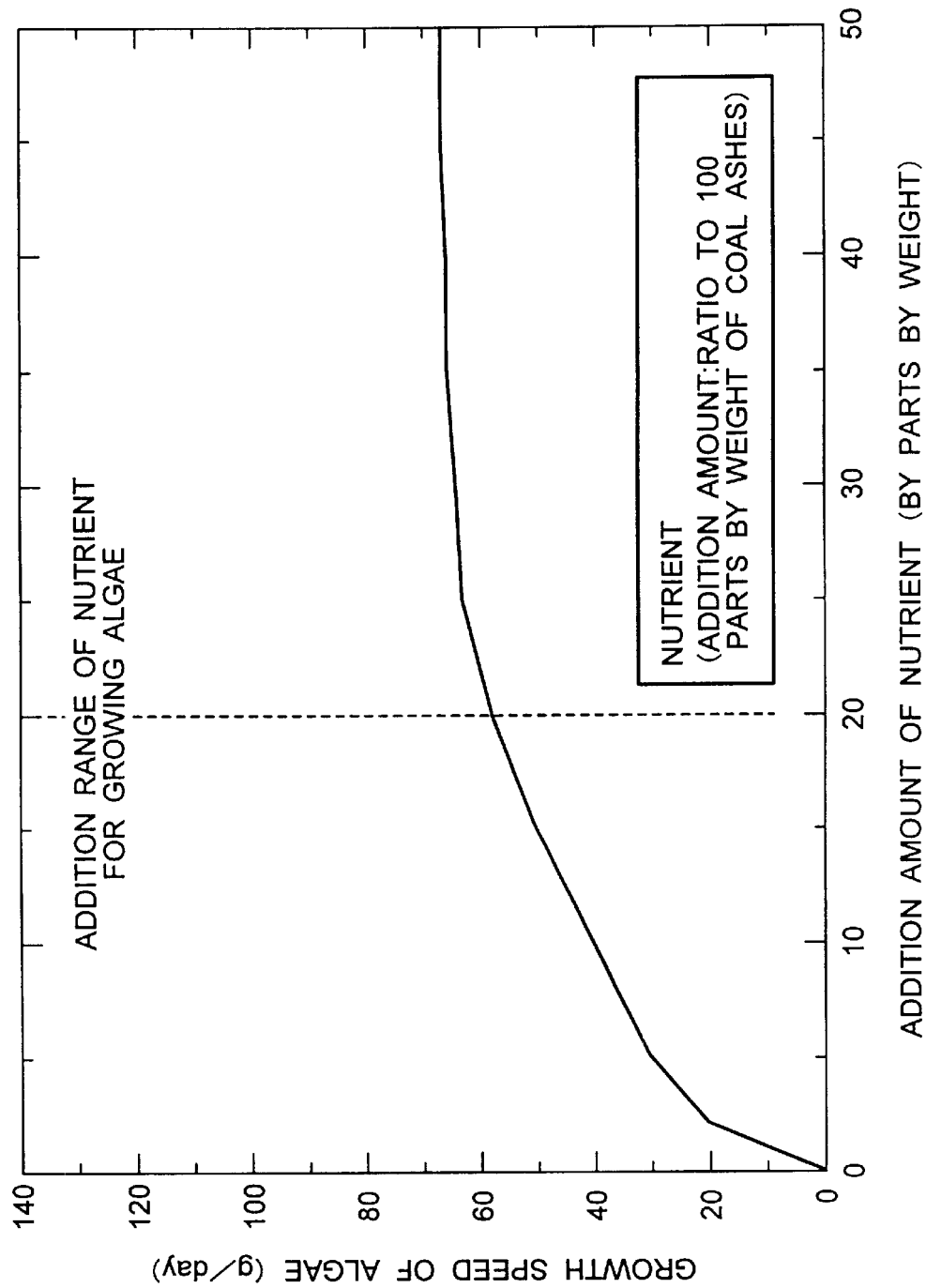
FIG. 9 is a diagram showing the relationship between an addition amount of a nutriment supply agent and the growth speed of the algae in the algae cultivating medium as set forth in Embodiment 8.

Under the conditions of Embodiment 8-1, the adding amount of iron phosphate+sodium phosphate+sodium nitrate is varied to investigate the variation of the growth speed of the algae. The results are shown in FIG. 9. From FIG. 9, it can be seen that the growth speed of the algae does not saturate with respect to the increment of the algae cultivating nutriment amount. The result also shows that the addition amount is appropriate when the algae cultivating nutriment is 20 parts by weight or less relative to 100 parts by weight of inorganic material.

Embodiment 9

The tests to study effectiveness of various kinds of density decreasing materials were carried out under the identical conditions as Embodiment 1. The inorganic material and curing material were restricted to coal ashes and sodium silicate, respectively. With the standard molding step identical with Embodiment 1 other than the above, the molded bodies of the algae cultivating media were prepared.

The results are shown in Table 9. From these results, it is confirmed that the molded bodies of the algae cultivating media that can float on water and multiply the algae can be obtained by using Shirasu and compounds thereof, granular pumice stone, and the mixture thereof other than pearlite as the density decreasing material.

Further, the effect of the difference of molding method with pearlite and Shirasu added as the density decreasing material, respectively, was tested. The tests are carried out with the method identical with the aforementioned Embodiments 2 to 5. The influence due to the difference of the molding steps is confirmed and the results are shown together in table 9.

TABLE 9

Results of application of various kinds of density decreasing materials

| | Run No. | | | | | | | | | |
|---|---|---|---|---|---|---|---|---|---|---|
| | 9-1 | 9-2 | 9-3 | 9-4 | 9-5 | 9-6 | 9-10 Disintegration molding | 9-11 Rolling molding | 9-12 Mixing molding | Note |
| Molding method | | | Standard molding | | | | | | | |
| Coal ashes | 100 | 100 | 100 | 100 | 100 | 100 | 100 | 100 | 100 | Inorganic material |
| Cement | 0 | 0 | 0 | 0 | 0 | 0 | 0 | 0 | 0 | Curing material |
| Sodium silicate | 5 | 5 | 5 | 5 | 5 | 5 | 5 | 5 | 5 | Curing material |
| Pearlite | 30 | 0 | 0 | 0 | 0 | 15 | 30 | 30 | 30 | Density decreasing material |
| Shirasu | 0 | 30 | 0 | 0 | 0 | 0 | 0 | 0 | 0 | Density decreasing material |
| Shirasu balloon | 0 | 0 | 30 | 0 | 0 | 15 | 0 | 0 | 0 | Density decreasing material |
| Alumina powder | 0 | 0 | 0 | 30 | 0 | 0 | 0 | 0 | 0 | Density decreasing material |
| Granular pumice stone | 0 | 0 | 0 | 0 | 20 | 0 | 0 | 0 | 0 | Density decreasing material |
| Nutriment supply material | | | 11: (sodium phosphate 5, iron phosphate 1, sodium nitrate 5) | | | | | | | |
| Density | 0.85 | 0.85 | 0.85 | 0.85 | 0.8 | 0.85 | 0.85 | 0.85 | 0.85 | Unit: g/cm³ |
| Floatation on water | Floating | Floating | Floating | Floating | Floating | Floating | Floating | Floating | Floating | |

| | Run No. | | | | | | | | | |
|---|---|---|---|---|---|---|---|---|---|---|
| Molding method | 9-13 Extrusion molding | 9-14 Compression molding | 9-15 Disintegration molding | 9-16 Rolling molding | 9-17 Mixing molding | 9-18 Extrusion molding | 9-19 Compression molding | Reference Standard | Reference molding | Note |
| Coal ashes | 100 | 100 | 100 | 100 | 100 | 100 | 100 | 100 | 100 | Inorganic material |
| Cement | 0 | 0 | 0 | 0 | 0 | 0 | 0 | 0 | 0 | Curing material |
| Sodium silicate | 5 | 5 | 5 | 5 | 5 | 5 | 5 | 5 | 5 | Curing material |
| Pearlite | 30 | 30 | 0 | 0 | 0 | 0 | 0 | 15 | 0 | Density decreasing material |
| Shirasu | 0 | 0 | 30 | 30 | 30 | 30 | 30 | 0 | 0 | Density decreasing material |
| Shirasu balloon | 0 | 0 | 0 | 0 | 0 | 0 | 0 | 0 | 0 | Density decreasing material |
| Alumina powder | 0 | 0 | 0 | 0 | 0 | 0 | 0 | 0 | 0 | Density decreasing material |
| Granular pumice stone | 0 | 0 | 0 | 0 | 0 | 0 | 0 | 0 | 0 | Density decreasing material |
| Nutriment supply material | | | 11: (sodium phosphate 5, iron phosphate 1, sodium nitrate 5) | | | | | | | |
| Density | 0.85 | 0.85 | 0.85 | 0.85 | 0.85 | 0.85 | 0.85 | 0.95 | 1.5 | Unit: g/cm³ |
| Floatation on water | Floating | Floating | Floating | Floating | Floating | Floating | Floating | Floating | Not floating | |

Note:
The unit of the compounding ratio in the table is weight ratio.

As obvious from these results, all of the obtained molded bodies can be regarded as almost identical with the cases where the standard molding step is applied. It is confirmed that the molded bodies have the densities of 1 g/cm³ or less and can float on water and can grow and increase algae. From these results, it is confirmed that the addition of the density decreasing material is effective and adequate regardless of the difference of the molding method.

Figure 10:
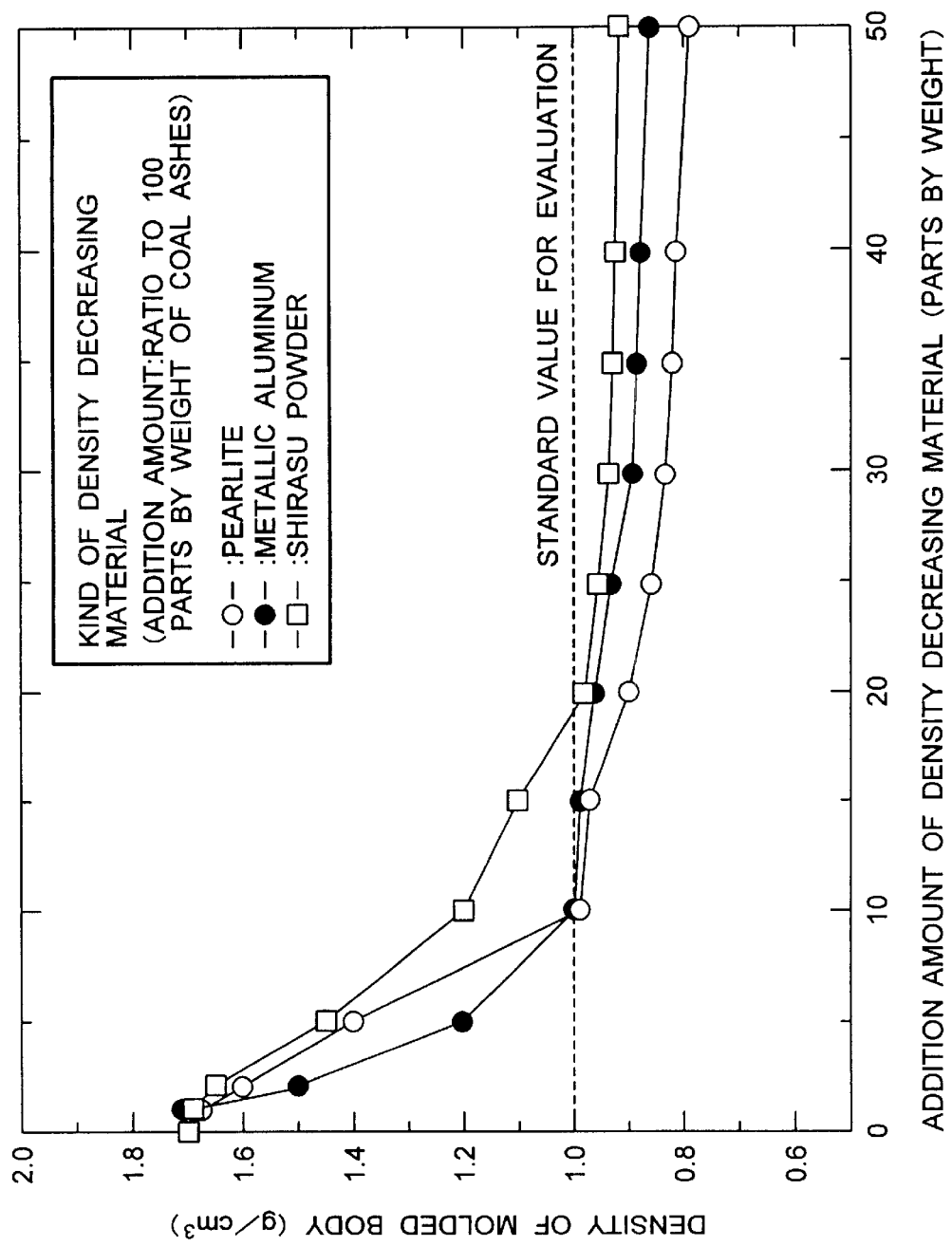
FIG. 10 is a diagram showing the relationship between an addition amount of density decreasing material and the density of the algae cultivating medium in the standard molding method as set forth in Embodiment 9.

The density change of the molded bodies varying addition amounts of pearlite, Shirasu and alumina powder were investigated under the respective conditions of the Embodiment runs 9-2, 9-3 and 9-5. The result is shown in FIG. 10.

From this results, it can be seen that the densities of the molded bodies are made 1 g/cm$^3$ or less and the molded bodies can float on water by adding 10 parts by weight or more of the density decreasing material relative to 100 parts by weight of the inorganic material.

Figure 11:
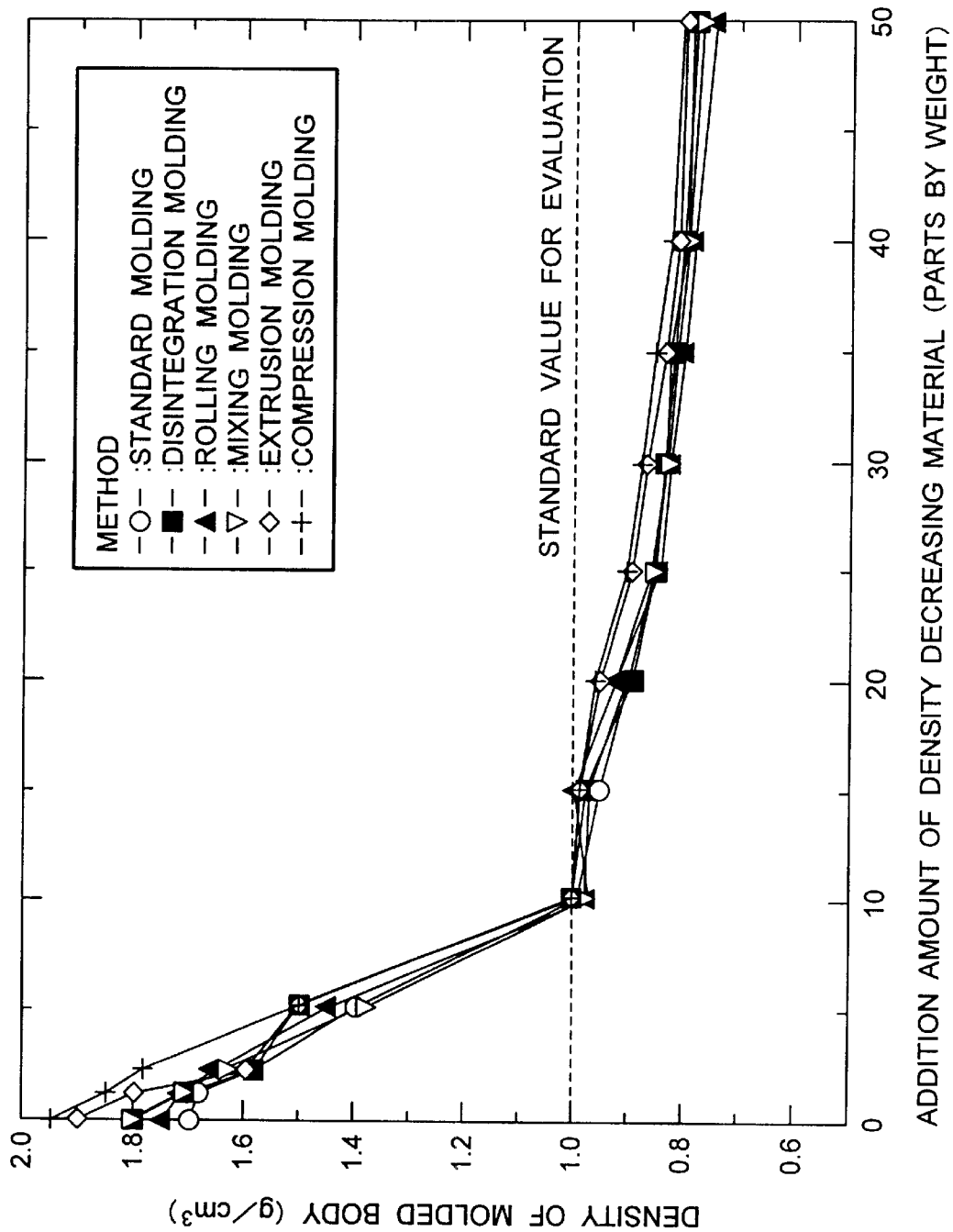
FIG. 11 is a diagram showing the relationship between an addition amount of density decreasing material and the density of the algae cultivating medium in the various kinds of molding methods as set forth in Embodiment 9.

Further, the effect of the difference of the molding method upon the molded body density was examined using pearlite as the density decreasing material. The results are shown in FIG. 11. From this result, we can find that the difference of the molding steps does not cause appreciable change to the density of the molded bodies. The density of the molded bodies decreases down to 1 g/cm$^3$ or less by adding 10 parts by weight or more of the density decreasing material.

Embodiment 10

Figure 12:
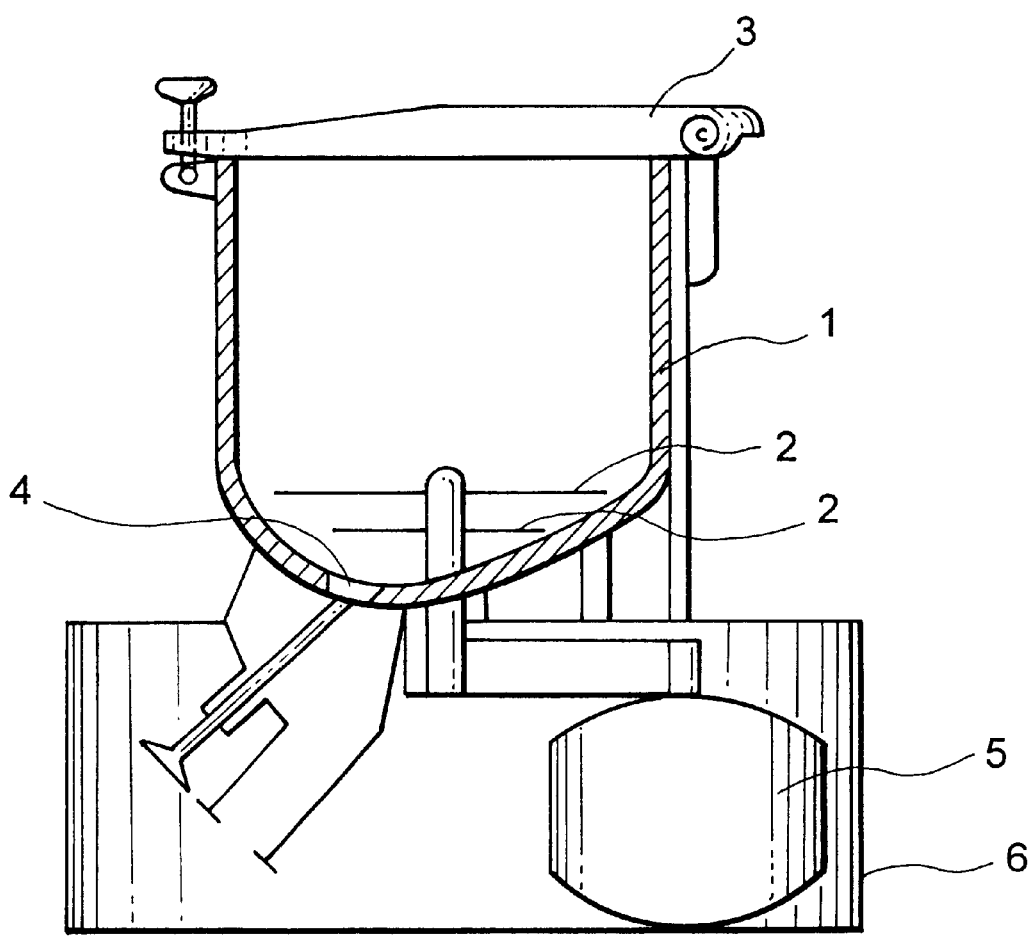
FIG. 12 is a cross-section showing diagrammatically a Henshel-type mixer in which, in the manufacturing process of the algae cultivating nutriment as set forth in Embodiment 11, the bottom portion of a mixing tank is tilted towards an exhausting outlet.

The effect of the difference of the type of mixers was examined. Coal ashes were mixed with a curing material and density decreasing material and algae cultivating nutriment and water, under the conditions identical with the aforementioned Embodiment 1 Run 1-1. The mixers used for this embodiment were two types each of high-speed blade mixers having peripheral velocity of 5 m/s or more and middle speed mixers having peripheral velocity of less than 5 m/s. The capacity of the mixing tank of every mixer was 20 L (liter) and the volume of the mixture in every mixer was adjusted to 10 L. The results are shown in Table 11. For each of these, two kinds of the standard type mixers shown in FIG. 2, and another type of mixers where bottom of the mixing tanks were tilted towards the exhaust outlet shown a schematic cross-section view in FIG. 12. Four mixers all together were used for the Embodiment and a wheel mixer for an example for comparison. In FIG. 12, reference numeral 1 denotes a mixing tank, reference numeral 2 denotes agitating blades, reference numeral 3 denotes a cover of the tank, reference numeral 4 denotes an exhaust outlet, reference numeral 6 denotes a table and reference numeral 7 denotes a tilting bottom of the mixing tank. The results of the mixing are shown in Table 10.

The mixture after mixing was exhausted from the mixer. The exhaust rate was obtained from the exhausted weight and the charged weight. The exhaust rates of the high-speed and middle-speed mixer of the type of which bottoms of the mixing tanks were tilted towards the exhaust outlet are 99.5% by weight, whereas the mixers of standard type give the exhaust rate of 95% for both the high-speed and middle-speed mixers. The remarkably high exhaust rates of the tilted type mixers seem to be due to the tilted bottom structure in which the mixture is pushed out by their own weight, whereas the standard type mixers do not have such structure for pushing out the mixture from the clearance portion below the rotating blades where the mixture is liable to remain. On the other hand, in the wheel-type mixer, the blocks are stuck to the rotating blades to cause deterioration of the exhaust rate, resulting in 80% by weight.

Subsequently, 10 L of water is poured into the mixing tank followed by rotation of 1 min. Thereafter, the cleaning water is exhausted. The cleansed state is visually observed. It was found that the high-speed blade type mixer could cleanse with excellence, however, in the standard type mixer, the cleaning water remained at the clearance portion below the rotating blades. On the other hand, in the middle-speed blade type mixer, a little mixture remained sticking to the wall surface of the mixing tank and the surface of the rotating blades. High-pressure water of a pressure of approximately 5 MPa is tried to spray, resulting in excellent cleaning off. In the wheel type mixer, even after the initial cleaning, a considerable amount of the mixture cannot wash off even spraying of the high-pressure water. Manual washing in combination was necessary to remove the remained mixture.

From the above results, the high-speed blade type mixer is suitable for the purpose of mixing uniformly a large amount of mixture, and for good exhaustion and cleaning, the bottom portion of the mixing tank tilt towards the exhaust outlet is desirable.

Embodiment 11

Manufacturing of molded bodies having a cavity portion inside thereof was carried out by using extrusion molding.

TABLE 10

| | Run No. | | | | |
|---|---|---|---|---|---|
| | 10-1 | 10-2 | 10-3 | 10-4 | 10-5 |
| Mixer | High-speed blade type | | Middle-speed blade type | | Wheel type |
| | Standard type | Mixing tank with a tilted bottom | Standard type | Mixing tank with a tilted bottom | |
| Mixing ability | Excellent (mixing time: 5 min) | Excellent (mixing time: 5 min) | Excellent (mixing time: 5 min) | Excellent (mixing time: 5 min) | Can't obtain uniform mixture (mixing time: 30 min) |
| Exhaust rate (wL %) | 95% | 99.5% | 95% | 99.5% | 80% |
| Cleaning ability | Excellent (a little residue at the clearance) | Excellent | a little residue, necessity of high pressure water, a little residue at the clearance | a little residue, necessity of high pressure water | residue of precipitate, necessity of high pressure water |

Exhaust rate = Amount of exhaust/Input amount × 100

The Table 10 shows that whereas the high-speed mixer and middle-speed mixer can obtain a uniform mixture with only 5-min mixing, whereas the wheel-type mixers require more than 30 min. In the case of the wheel-type mixer, the mixture was not uniform and contained lumps.

Figure 13:
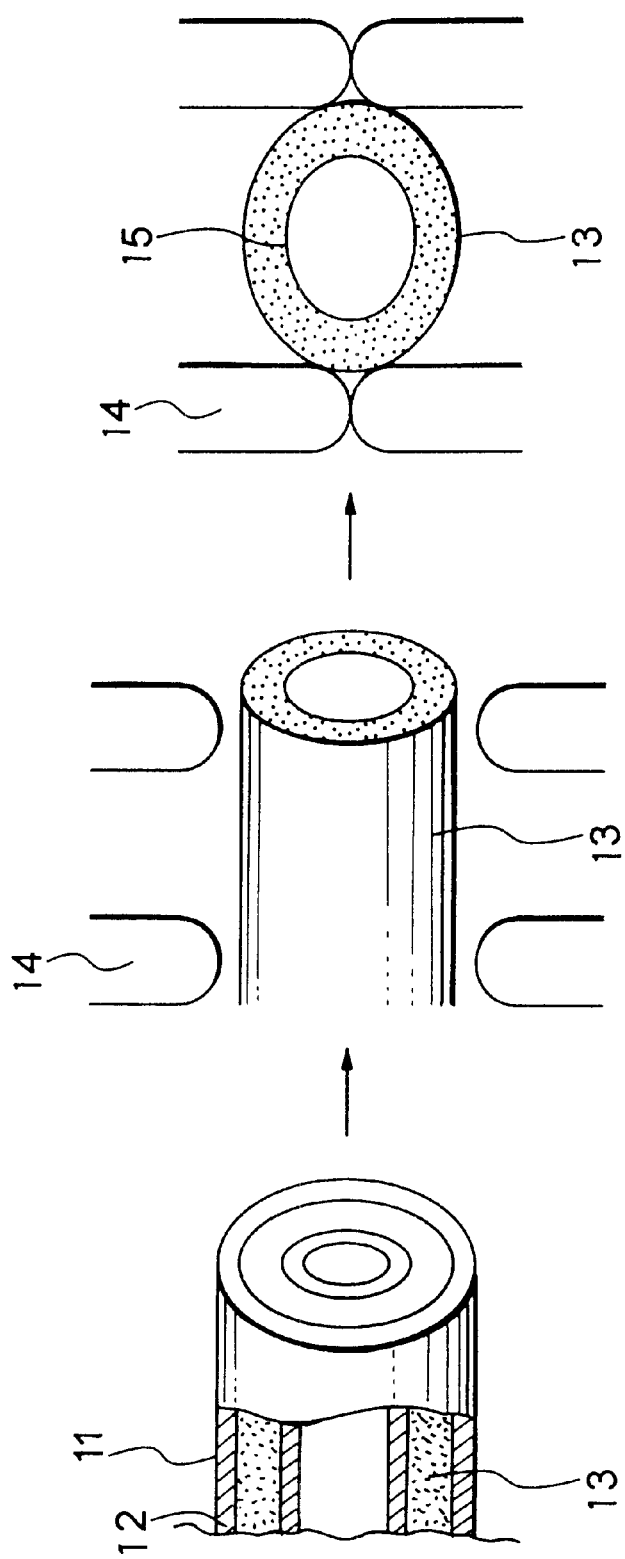
FIG. 13 is a schematic diagram showing diagrammatically an extrusion molding method for manufacturing a molded body having a cavity portion inside thereof as set forth in Embodiment 12.

Schematic diagram, which explains the present embodiment, is shown in FIG. 13. The present embodiment followed the step of extrusion molding described in Embodiment 4 except for no addition of the density decreasing material. Curing material (sodium silicate), algae cultivating nutriment (sodium phosphate, iron phosphate, sodium nitrate) and water with the inorganic material (coal ashes) were mixed by a high-speed blade type mixer. A raw material mixture of porous layer 13 was inserted between an outside tube 11 and an inside tube 12 of a double tube die and extruded to obtain cylindrical body. Both edges of the extruded body were compressed by using a press 14 to form a molded body having a cavity portion 15 inside thereof. The curing is conducted at a temperature of 110° C. for 24 hours. The size of the molded body was approximately 2 mm in a diameter of the cavity portion, approximately 5 mm in an outside diameter of the porous layer and approximately 1 cm long. The molded body could float on water for approximately 200 days.

Figure 14:
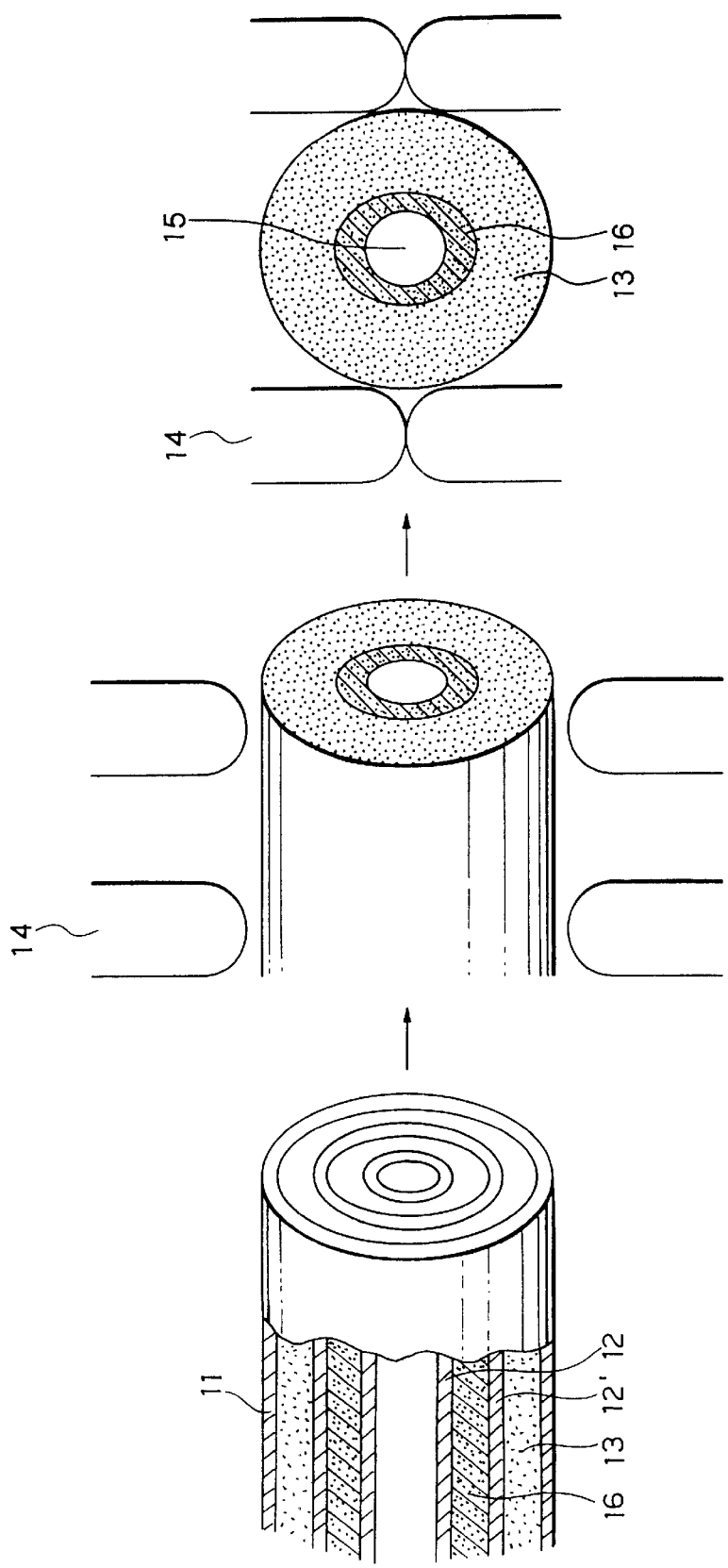
FIG. 14 is a schematic diagram showing diagrammatically an extrusion molding method for manufacturing a molded body having a cavity portion and a layer of low permeability inside thereof as set forth in Embodiment 12.

Another embodiment for a molded body having a cavity portion inside thereof with a layer of low water permeability manufactured is shown in FIG. 14. The same portions as Embodiment 13 have the same reference numerals in FIG. 14. In the embodiment illustrated in FIG. 13, the molded body precipitates when water that permeates through the molded body goes inside of the cavity portion and accumulates inside thereof. However, the embodiment illustrated in FIG. 14 that placed a layer 16 of low water permeability protecting the water penetration between the porous layer 13 and the cavity portion 5, can float for much longer time.

Using a die constituting of a three-fold tube illustrated in FIG. 14, a cylindrical body was extruded charging the porous material 13 between an outermost tube 11 and an intermediate tube 12' and the low water permeability material 6 between the intermediate tube 12' and the innermost tube 13, respectively. As the low water permeability material coal ashes, incineration ashes, montmorillonite, kaolinite, cement, water glass, lime, and gypsum were used. The molded bodies were 2 mm in diameter of the cavity portion, 1 mm in thickness of the layer of low permeability, approximately 6 mm in outer diameter of the porous layer and approximately 10 mm in length. The other steps were carried out identically with the case for FIG. 13.

The molded bodies were water permeated through the porous layer was remarkably retarded in the permeation speed thereof by the layer of low water permeability. Thereby, the molded bodies could float on water for a long enough period even the molded body did not contain density decreasing material and could supply the nutriment for aquatic life such as algae.

The molded bodies manufactured had floated for more than one year and are still floating on water at the time of this application.

Embodiment 12

Progress of the curing was studied for each case during curing process. The molded bodies formed according to the standard step identical with Embodiment 1 was cured under heating and heated to cure in vapor. The results are shown in Table 11.

TABLE 11

Effect of Heat-treatment during Curing

| Molding method | Run No. | | | | | | | | | | | | Note |
|---|---|---|---|---|---|---|---|---|---|---|---|---|---|
| | 11-1 | 11-2 | 11-3 | 11-4 | 11-5 | 11-6 | 11-7 Disintegration molding | 11-8 Rolling molding | 11-9 Mixing molding | 11-10 Extrusion molding | 11-11 Compression molding | Reference Standard molding | |
| | Standard molding | | | | | | | | | | | | |
| Coal ashes | 100 | 100 | 100 | 100 | 0 | 0 | 100 | 100 | 100 | 100 | 100 | 100 | Inorganic material |
| Incineration ashes | 0 | 0 | 0 | 0 | 100 | 100 | 0 | 0 | 0 | 0 | 0 | 0 | Inorganic material |
| Cement | 20 | 0 | 0 | 30 | 20 | 0 | 0 | 0 | 100 | 0 | 0 | 0 | Curing material |
| Sodium silicate | 0 | 5 | 0 | 0 | 0 | 5 | 5 | 5 | 5 | 5 | 5 | 5 | Curing material |
| Pearlite | 30 | 30 | 30 | 30 | 30 | 30 | 30 | 30 | 30 | 30 | 30 | 30 | Density decreasing material |
| Sodium phosphate + iron phosphate + sodium nitrate | 11 | 11 | 11 | 11 | 11 | 11 | 11 | 11 | 11 | 11 | 11 | 11 | Algae cultivating nutriment |
| Density | 0.95 | 0.9 | 0.9 | 0.95 | 0.95 | 0.9 | 0.9 | 0.9 | 0.9 | 0.9 | 0.9 | 0.9 | Unit: g/cm$^3$ |
| Floatation on water | Floating | Floating | Floating | Floating | Floating | Floating | Floating | Floating | Floating | Floating | Floating | Floating | |
| Increase of algae | Increased | Increased | Increased | Increased | Increased | Increased | Increased | Increased | Increased | Increased | Increased | Not increased | Carried out in a water tank |

TABLE 11-continued

Effect of Heat-treatment during Curing

| Heating method | Heated at 100° C. or more | In vapor of 100° C. or more | Heated at 100° C. or more | Heated at 100° C. or more | Normal temperature |
|---|---|---|---|---|---|
| Manufacturing time | | Within one day | | Within one day | Two days |

Note:
The unit of the compounding ratio in the table is weight ratio.

From these results, it was found that the curing took place faster and therefore the manufacturing time shorter when the molded body were cured while heating, or while heating in vapor, compared with when such heating treatments were not implemented. Further, tests were carried out to know the influence of the difference of the molding methods using each method described in Embodiments 2 to 5. These results are also shown in Table 11. As obvious from these results, it was confirmed that the curing took place within a day regardless of the difference of the molding method when heated at a temperature of 100° C. or more. In this embodiment a vapor from once-through vapor was used. Waste heat from these plants can be used advantageously in cost when a molding apparatus is disposed to a thermal power plant or a waste incinerator.

The embodiments described in the present specification are only illustrative and not restrictive. The range of the present invention are shown in following claims and all modifications being included in the claims are included in the scope of the present invention.

What is claimed is:

1. A method of manufacturing an algae cultivating medium, comprising the steps of:
   mixing a raw material comprising an inorganic material, a curing material, and an algae cultivating nutriment to form a mixture;
   molding the mixture into a molded body; and
   curing the molded body;
wherein the steps are carried out so that the algae cultivating medium is water floatable.

2. The method of manufacturing the algae cultivating medium as set forth in claim 1, wherein the molding step comprises the steps of:
   charging the mixture into a mold to form a preparatory molded body, and
   disintegrating the preparatory molded body to fine molded bodies.

3. The method of manufacturing the algae cultivating medium as set forth in claim 1, wherein a high-speed blade mixer is used at the mixing step and the molding step comprises a step of agitating the mixture while spraying liquid selected from the group consisting of water and an aqueous solution of a curing material to the mixture.

4. The method of manufacturing the algae cultivating medium as set forth in claim 3, wherein the agitation molding step is implemented in the high-speed blade mixer that is used for the mixing step.

5. The method of manufacturing the algae cultivating medium as set forth-in claim 3, wherein the curing of the molded body is conducted at a temperature of 100° C. or more.

6. The method of manufacturing the algae cultivating medium as set forth in claim 1, wherein the molding step comprises a step of extruding a molded body by transferring the mixture to a die.

7. The method of manufacturing the algae cultivating medium as set forth in claim 6, wherein the die is a double tube die and the extrusion molding step comprises the steps of:
   transferring the mixture between an inner wall of an outside tube and an outer wall of an inside tube of the double tube,
   extruding the mixture, and
   sealing both edges thereof by cutting to form a molded body having a porous outside material layer and an inside cavity portion thereof.

8. The method of manufacturing the algae cultivating medium as set forth in claim 7, further comprising the step of providing a low water permeability layer compared with the porous outside material layer between the porous outside material layer and the inside cavity portion.

9. The method of manufacturing the algae cultivating medium as set forth in claim 8, wherein the step of providing the low water permeability layer is conducted by extruding by charging the porous material between an outermost tube and an intermediate tube of a die constituted by a three-fold tube and low water permeability material between the intermediate tube and an innermost tube thereof, and thereafter compressing and sealing off both edges thereof.

10. The method of manufacturing the algae cultivating medium as set forth in claim 9, herein the low water permeability layer contains at least one low water permeability material selected from the group consisting of coal ashes, incineration ashes, montmorillonite, kaolinite, cement, water glass, lime and gypsum.

11. The method of manufacturing the algae cultivating medium as set forth in claim 1, wherein the molding step comprises a step of compressing the mixture for forming a molded body.

12. The method of manufacturing the algae cultivating medium as set forth in claim 1, wherein the inorganic material is at least one selected from the group consisting of coal ashes, incineration ashes, sands, crushed shells, and diatomite.

13. The method of manufacturing the algae cultivating medium as set forth in claim 12, wherein the inorganic material is subjected to a treatment for reducing or eliminating a component that pollutes environment.

14. The method of manufacturing the algae cultivating medium as set forth in claim 1, wherein the curing material is at least one selected from the group consisting of cement, water glass, lime and gypsum.

15. The method of manufacturing the algae cultivating medium as set forth in claim 14, wherein the curing material contains algae cultivating nutriment as a constituent component.

16. The method of manufacturing the algae cultivating medium as set forth in claim 1, wherein the algae cultivating nutrient is at least one selected from the group consisting of a phosphor nutrient, a nitrogen nutrient and an iron nutrient.

17. The method of manufacturing the algae cultivating medium as set forth in claim 1, wherein the raw material comprises at least 5 parts by weight of the curing material, and-not more than 20 parts by weight of the algae cultivating nutriment, relative to 100 parts by weight of the inorganic material.

18. The method of manufacturing the algae cultivating medium as set forth in claim 1, wherein the high-speed blade mixer comprises a mixing tank of which bottom portion is tilted towards an exhaust outlet.

19. The method of manufacturing the algae cultivating medium as set forth in claim 1, wherein the curing step comprises a step of curing under heating and a heat source is a waste heat of a plant selected from the group consisting of a thermal electric power plant or a waste incinerator.

20. The method of manufacturing the algae cultivating medium as set forth in claim 1, wherein the raw material further comprises a density decreasing material.

* * * * *